United States Patent [19]

Baschang et al.

[11] Patent Number: 4,666,886
[45] Date of Patent: May 19, 1987

[54] NOVEL PEPTIDE DERIVATIVES

[75] Inventors: Gerhard Baschang, Bettingen, Switzerland; Albert Hartmann, Grenzach, Fed. Rep. of Germany; Oskar Wacker, Basel, Switzerland

[73] Assignee: Ciba-Geigy Corporation, Ardsley, N.Y.

[21] Appl. No.: 756,146

[22] Filed: Jul. 17, 1985

Related U.S. Application Data

[63] Continuation-in-part of Ser. No. 724,495, Apr. 18, 1985, abandoned, which is a continuation of Ser. No. 572,281, Jan. 20, 1984, abandoned.

[30] Foreign Application Priority Data

Jan. 25, 1983 [CH] Switzerland .................. 398/83

[51] Int. Cl.$^4$ .................. A61K 37/02; C07K 5/08; C07K 5/10; C07K 7/06
[52] U.S. Cl. .................. 514/17; 514/18; 530/329; 530/330; 530/331
[58] Field of Search .................. 514/19, 17, 18; 530/329, 330, 331

[56] References Cited

U.S. PATENT DOCUMENTS 4,439,425  3/1984  Tarcsay et al. .................. 514/19

FOREIGN PATENT DOCUMENTS 0000330  8/1981  European Pat. Off. .................. 514/19

OTHER PUBLICATIONS

Hantke, et al., Eur. J. Biochem., 34, 284–296, (1973).

Primary Examiner—Delbert R. Phillips
Attorney, Agent, or Firm—Karl F. Jorda; Michael W. Glynn; Irving M. Fishman

[57] ABSTRACT

The invention relates to lipopeptides of the formula I,

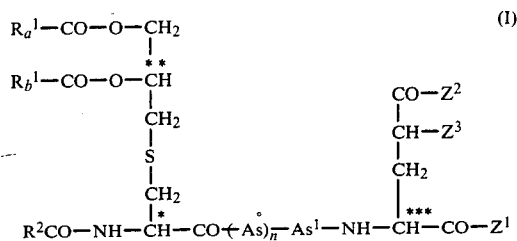

in which
each of $R_a^1$ and $R_b^1$, independently of the other, represents an aliphatic or cycloaliphatic-aliphatic hydrocarbon radical having from 7 to 21 carbon atoms that is optionally substituted by oxygen functions, or one of the radicals $R_a^1$—CO— and $R_b^1$—CO— represents hydrogen and the other of the radicals $R_a^1$—CO— and $R_b^1$—CO— represents an acyl radical, wherein $R_a^1$ and $R_b^1$ have the meanings given above,
$R^2$ represents an aliphatic or cycloaliphatic-aliphatic hydrocarbon radical having from 1 to 21 carbon atoms that is optionally substituted by oxygen functions,
$n=0$ or 1,
$As°$ represents a radical of the formula —O—Kw—CO— or —NH—Kw—CO— wherein Kw represents an aliphatic hydrocarbon radical having a maximum of 12 carbon atoms,
$As^1$ represents a D- or L-α-amino acid,
each of $Z^1$ and $Z^2$, independently of the other, represents hydroxy or the N-terminal radical of a D- or L-α-aminocarboxylic acid, of an amino-lower alkanesulphonic acid or of a peptide having a maximum of 6 amino acids from the group consisting of D- or L-α-aminocarboxylic acids and amino-lower alkanesulphonic acids, and
$Z^3$ represents hydrogen or —CO—$Z^4$ wherein $Z^4$ represents hydroxy or the N-terminal radical of a D- or L-α-amino acid, of an amino-lower alkanesulphonic acid or of a peptide having a maximum of 6 amino acids from the group consisting of D- or L-α-aminocarboxylic acids and amino-lower alkanesulphonic acids,
and the amides and esters of such compounds that contain carboxy groups.

The novel lipopeptides have an immunity-stimulating action.

77 Claims, No Drawings

NOVEL PEPTIDE DERIVATIVES

This is a continuation-in-part application of U.S. patent application Ser. No. 724,495 filed Apr. 18, 1985 now abandoned which in turn is a continuation of U.S. patent application Ser. No. 572,281 filed Jan. 20, 1984, now abandoned.

The present invention relates to novel lipopeptides and especially to compounds of the formula I

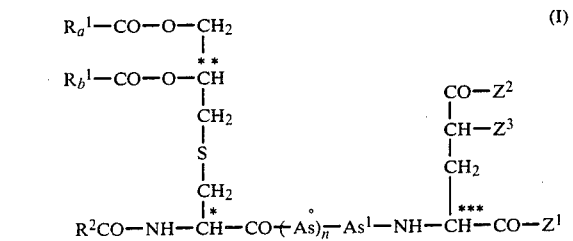

* = R
** = R or S
*** = R in which
each of $R_a^1$ and $R_b^1$, independently of the other, represents an aliphatic or cycloaliphatic-aliphatic hydrocarbon radical having from 7 to 21 carbon atoms that is optionally substituted by oxygen functions, or
one of the radicals $R_a^1$-CO- and $R_b^1$-CO- represents hydrogen and the other of the radicals $R_a^1$-CO- and $R_b^1$-CO- represents an acyl radical, wherein $R_a^1$ and $R_b^1$ have the meanings given above,
$R^2$ represents an aliphatic or cycloaliphatic-aliphatic hydrocarbon radical having from 1 to 21 carbon atoms that is optionally substituted by oxygen functions,
n=0 or 1,
As° represents a radical of the formula -O-Kw-CO- or -NH-Kw-CO- wherein Kw represents an aliphatic hydrocarbon radical having a maximum of 12 carbon atoms,
$As^1$ represents a D- or L-α-amino acid,
each of $Z^1$ and $Z^2$, independently of the other, represents hydroxy or the N-terminal radical of a D- or L-α-aminocarboxylic acid, of an amino-lower alkanesulphonic acid or of a peptide having a maximum of 6 amino acids from the group consisting of D- or L-α-aminocarboxylic acids and amino-lower alkanesulphonic acids, and
$Z^3$ represents hydrogen or -CO-$Z^4$ wherein $Z^4$ represents hydroxy or the N-terminal radical of a D- or L-α-amino acid, of an amino-lower alkanesulphonic acid or of a peptide having a maximum of 6 amino acids from the group consisting of D- or L-α-aminocarboxylic acids and amino-lower alkanesulphonic acids,
and the amides and esters of such compounds that contain carboxy groups, wherein the centres of asymmetry designated by *,  and * have the absolute configurations indicated, and the configuration at an asymmetric carbon atom carrying the group $Z^3$ may be R or S, and corresponding diastereoisomeric mixtures, as well as salts of such compounds having at least one salt-forming group and optionally complex salts of these compounds. The invention relates also to processes for the manufacture of these lipopeptides and to pharmaceutical preparations containing one or more of these compounds together with a pharmaceutical carrier and optionally together with other pharmaceutical compounds. In the following, unless the context indicates otherwise, "lipopeptides of the formula I" shall be understood to include also all of the above-mentioned derivatives, diastereoisomeric mixtures and salts thereof.

The invention relates especially to the above-mentioned compounds in which $R_a^1$ and $R_b^1$ have the same meanings and each represents an aliphatic or cycloaliphatic-aliphatic hydrocarbon radical having from 7 to 21 carbon atoms that is optionally substituted by oxygen functions, each of $Z^1$ and $Z^2$, independently of the other, represents hydroxy or the N-terminal radical of a D- or L-α-amino acid or of a peptide having a maximum of 6 D- or L-α-amino acids, and $Z^3$ represents hydrogen or -CO-$Z^4$ wherein $Z^4$ represents hydroxy or the N-terminal radical of a D- or L-α-amino acid or of a peptide having a maximum of 6 D- or L-α-amino acids.

α-Amino acids are preferably naturally occurring L-α-aminocarboxylic acids and the antipodes thereof of the D-series. Where no details are given, the L-configuration is intended. An amino acid $As^1$ is preferably selected from the group comprising glycine (Gly), alanine (Ala), α-methyl-alanine (αMeAla), N-methyl-alanine (MeAla), serine (Ser), α-aminobutyric acid (Abu), valine (Val) and Leucine (Leu), an amino acid in the radical $Z^1$ is preferably selected from the group comprising lysine (Lys), ornithine (Orn), a,a'-diamino-pimelic acid (Dpm), Gly, Ala, D-Ala or D-asparagine (D-Asn) and an amino acid in the radicals $Z^2$ or $Z^4$ is preferably selected from the group comprising Lys, Orn, Dpm, lanthionine (Lan), Gly, Ala or D-Ala, a peptide radical $Z^1$, $Z^2$ or $Z^4$ preferably consisting of amino acids selected in such a manner, preferably from 2 such amino acids.

In this application, in accordance with the internationally recognised rules on nomenclature, the abbreviations for the amino acids, for example the above-mentioned abbreviations, indicate the free acid and, unless specified otherwise, the L-configuration. The α-amino group is to be imagined at the left-hand side of the abbreviation, the carboxy group at the right-hand side. The absence of one hydrogen atom from the α-amino group is characterised by a hyphen positioned at the left of the abbreviation of the amino acid, and the absence of two hydrogen atoms by two hyphens positioned at the left. The absence of a hydroxy group from the carboxy group is expressed by a hyphen positioned at the right. Substituents in the side chain of amino acids are placed in brackets directly after the amino acid symbol. Thus, for example, palmitoyl-Cys(2[R],3-dilauroyloxy-propyl)-Ala-D-Glu(OtBu)-NH2 represents N-palmitoyl-S-(2[R],3-dilauroyloxy-propyl)-cysteinyl-alanyl-D-isoglutaminyltert.-butyl ester.

An amino-lower alkanesulphonic acid is especially a ω-amino-lower alkanesulphonic acid, preferably a ω-amino-$C_{2-3}$-alkanesulphonic acid, such as, especially, taurine or, in addition, homotaurine.

According to the invention there are preferred lipopeptides of the formula (I) in which $As^1$ is selected from the group consisting of Gly, Ala, Ser, Abu, Val, MeAla, αMeAla and Leu, each of $Z^1$ and $Z^2$, independently of the other, represents a hydroxy group or the radical of a naturally occurring amino acid, and $Z^3$ represents hydrogen or the radical of a naturally occurring amino acid, and the amides and esters thereof (compound group IA), and especially those in which an amino acid radical $Z^1$ is selected from the group consisting of -Lys, -Orn, -Dpm, -Gly, -D-Ala, -D-Asn and -Ala, and each of the amino acid radicals $Z^2$ and $Z^4$, independently of the other, is selected from the group consisting of -Lys, -Orn, -Dpm, -Lan (lanthionine), -Gly and -Ala, and the esters and amides thereof (compound group IB).

In European Patent Specification No. 0 000 330, lipopeptides of the formula

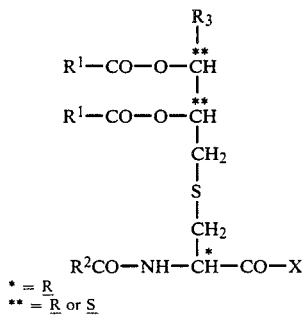

* = R
** = R or S are described in which each of $R^1$ and $R^2$ represents a saturated or unsaturated, aliphatic or mixed aliphatic-cycloaliphatic hydrocarbon radical having from 11 to 21 carbon atoms that is optionally also substituted by oxygen functions, $R_3$ represents hydrogen or the radical $R^1$-CO-O-CH$_2$- in which $R^1$ has the same meaning as above, and X represents a natural aliphatic amino acid bonded by a peptide linkage and having a free, esterified or amidated carboxy group, or an amino acid sequence of from 2 to 10 natural aliphatic amino acids of which the terminal carboxy group is in free, esterified or amidated form. These compounds have immunity-potentiating properties and are not lymphocytotoxic even at high concentrations. A peptide chain X in this case consists of a randomly ordered sequence of natural amino acids, whereas in the natural lipopeptides obtained by degradation from lipoproteins of the outer cell wall of *Escherichia coli* (cf., for example, Eur. J. Biochem. 34, 284–296 (1973)) only the sequence -Ser-Ser-Asn-Ala-Lys-OH is bonded to the "glycerylcysteine" moiety.

The amino acids making up the peptide sequence X in the mentioned European Patent Specification are the natural known classic building blocks of peptides and proteins belonging to the L-series. As can be seen from the above formula (I), by contrast the corresponding sequence in the lipopeptides according to the present invention contains as characteristic feature a D-amino acid, namely D-glutamic acid (D-Glu) or D-γ-carboxyglutamic acid (D-Gla) or the esters and amides thereof. It has been found, in accordance with the present invention, that such compounds possess a pharmacological activity that is superior to that of the compounds of the mentioned European Patent Specification. The compounds of the formula (I) and the mentioned derivatives, salts and complex salts thereof, at a dose of as low as 0.01 μg/ml, stimulate the proliferation, determined in vitro by thymidine incorporation, of mouse B-lymphocytes by up to 100-fold in comparison with control lymphocytes not stimulated, whereas in the case of the compounds of the mentioned European Patent this is not the case until 0.5 μg/ml and the extent of stimulation achieved is only 20- to 50-fold by comparison with the controls. According to the present invention the novel lipopeptides are already active at concentrations at which hitherto known B-cell mitogens (for example purified protein derivative=PPD or lipoprotein and lipopolysaccharide of *Escherichia coli*) do not yet exhibit any activity.

Moreover, the compounds are capable of activating rat and mouse alveolar macrophages in vitro, so that after 24 hours' incubation with the substance such macrophages are able to destroy tumour cells. If the compounds, incorporated in liposomes (multilamellar vesicles), are added to the alveolar macrophages, the compounds are capable, even at 0.2 μg/0.2 ml of culture, of inducing tumoricidal macrophages, whereas the compounds of the above-mentioned European Patent Specification are capable of doing this only when a dosage ten times higher is reached.

In in vivo models too the novel compounds are distinguished by high biological activity: NMRI mice are immunised by intraperitoneal injection of 10 μg of bovine serum albumin (BSA) on day 0. Serum samples are taken 8, 18 and 28 days later and tests are carried out, using a passive haemagglutination technique, to determine their content of anti-BSA antibodies. In the dosage used, BSA is sub-immunogenic for the receiver animals, that is to say it is not able to initiate any production of antibodies or is able to initiate only insignificant antibody production. In this test, the compounds according to the invention are able, on intraperitoneal administration of 0.1 mg/kg (administered on the day of immunisation), significantly to increase the production of antibodies against BSA. Special mention should be made of the good activity of the novel compounds when administered s.c., where they are effective at as little as 5 mg/kg.

The lipopeptides of the formula I exhibit strong prophylactic activity against infections caused by infective organisms, e.g. *Escherichia coli, Klebsiella pneumoniae, Streptococcus pneumoniae, Staphylococcus aureus, Streptococcus pyogenes* or *Pseudomonas aeruginosa*, as can be determined e.g. in mice:

In a typical test in order to determine the prophylactic activity against lower respiratory tract infections caused by *Klebsiella pneumoniae* or *Streptococcus pneumoniae* groups of mice are treated intranasally either 24 or 48 hours before challenge infection, with 0.05, 0.1 or 1.0 mg/kg of a lipopeptide of the formula I, e.g. with palmitoyl-Cys(2[R],3-dilauroyloxy-propyl)-Ala-D-Glu(Gly-taurine-sodium salt)-NH$_2$. In the untreated control group all mice die within 2 to 4 days with a severe pneumonic infection, whereas up to 70% of the treated mice survive the fourteenth day after infection.

In a typical test in order to determine the prophylactic activity against systemic infections caused by *Escherichia coli, Pseudomonas aeruginosa* or *Staphylococcus aureus* groups of mice are treated intraperitoneally and in the case of *E. coli* also subcutaneously and intravenously, either 24 or 48 hours before challenge infection with 1 or 10 mg/kg of a lipopeptide of the formula I, e.g. with palmitoyl-Cys(2[R],3-dilauroyloxy-propyl)-Ala-D-Glu-NH$_2$, palmitoyl-Cys(2[R],3-dilauroyloxy-propyl)-Ala-D-Glu-(Gly-taurine-sodium salt)-NH$_2$ or palmitoyl-Cys(2[R],3-dilauroyloxy-propyl)-Ala-D-Glu(Ala-taurine-sodium salt)-NH$_2$. In the untreated control group all mice die within 1 to 2 days with a severe infection, whereas up to 70 to 100% of the treated mice survive the fifth day after infection.

Some lipopeptides of the formula I, e.g. those containing at least one amino-lower alkanesulphonic acid, and the pharmaceutically acceptable acids thereof, e.g. palmitoyl-Cys(2[R],3-dilauroyloxy-propyl)-Ala-D-Glu(Gly-taurine-sodium salt)-NH$_2$, are excellently suitable both for the prophylaxis and treatment of virus infections as demonstrated, for example, by animal experiments. In these animal experiments animals, such as mice or guinea pigs, are infected by a wide variety of types of virus in a dose that is lethal for all or, preferably the large majority of untreated (control) animals, for example LD$_{80-90}$, and the course of the infection is observed in the untreated control animals compared with animals that are treated, e.g. orally or intranasally, before, at the same time as, or after the infection, with one of the above-mentioned lipopeptides or a pharmaceutically acceptable salt thereof.

These experiments demonstrate a significant antiviral action of the above-mentioned lipopeptides and their pharmaceutically acceptable salts even when administered in a single dose as low as 0.001 mg/kg. It is especially remarkable that a therapeutic effect still occurs on administration several days, for example 1 week, after infection.

Remarkable is also the broad viral spectrum against which the above-mentioned compounds are effective.

Said compounds can be used especially for the prophylaxis and treatment of diseases caused by the viruses specified in detail hereinafter [for nomenclature cf. J. L. Melnick, Prog. med. Virol. 26, 214–232 (1980) and 28, 208–221 (1982)]: DNA viruses with cubic symmetry and naked nucleocapsid, DNA viruses with enveloped virion and also RNA viruses with cubic, and those with helical, symmetry of the capsid.

Preferably, said compounds of the formula I are used in the case of DNA viruses with enveloped virion and cubic symmetry of the capsid, in the case of RNA viruses with cubic symmetry of the capsid and naked virion, and in the case of RNA viruses with helical symmetry of the capsid, in which the nucleocapsid casing is located at the surface membrane, but also in the case of Adenoviridae, Poxviridae and Coronaviridae, such as, especially human coronaviruses.

Said compounds of the formula I are used especially in the case of Herpesviridae, Picornaviridae and myxoviruses, but also in the case of mastadenoviruses, such as, especially, human adenoviruses, in the case of Chordopoxvirinae, such as, chiefly, orthopoxviruses, such as, especially, for example, vaccinal viruses, in the case of Reoviridae, chiefly (especially human) rotaviruses, and also in the case of Caliciviridae and Rhabdoviridae, such as, especially, vesiculoviruses in humans as well as horses, cows and pigs.

Said compounds of the formula I are mainly used in the case of Alphaherpesvirinae like Varicellaviruses, for example human varicellazoster viruses, rhinoviruses, cardioviruses and Orthomyxoviriadae, but also in the case of Beta-herpesvirinae, such as, especially, human cytomegaloviruses, in the case of aphthoviruses, especially aphthoviruses of cloven-hoofed animals, such as, chiefly, cows, and in the case of Paramyxoviridae, such as, especially, pneumoviruses, for example respiratory syncytial viruses in humans, and such as, in addition, morbilliviruses or paramyxoviruses, such as parainfluenza viruses, for example human parainfluenza viruses, including Sendai viruses, as well as in the case of arboviruses or vesiculoviruses, for example vesicular stomatitis viruses.

Above all said compounds of the formula I are used for simplex viruses, for example human herpes simplex viruses of types 1 and 2, and in the case of human encephalomyocarditis viruses, and most especially in the case of influenza viruses, such as mainly influenza A and influenza B viruses.

The dosage of the active ingredient depends, inter alia, on the species of the warm-blooded animal, the defensive condition of the organism, the mode of administration and the nature of the virus. There is no especially pronounced relationship between dosage and action.

In the case of virus infections a single dose of from approximately 0.01 mg to approximately 10 mg, preferably from 0.05 to 2 mg, for example 0.5 mg, of active ingredient is administered to a warm-blooded animal of approximately 70 kg body weight, for example a human. If required, the administration of this dose can be repeated.

The novel lipopeptides according to the present invention are of low toxicity: even intraperitoneal administration five times in a dosage of 10 mg/kg/day on five consecutive days is tolerated by mice without apparent symptoms, and in the case of subcutaneous administration the compounds are non-toxic up to doses of 300 mg/kg. Since the doses necessary for the immunity stimulation are very low, the therapeutic range of the novel compounds is extremely wide.

The novel lipopeptides according to the present invention can be used as adjuvants in admixture with vaccines to improve the results of vaccination, and to improve the protection imparted by humoral antibodies and/or by cellular immunity against infection by bacterial, viral or parasitic pathogens.

The novel lipopeptides may be used to promote immune reactions in humans and animals. Accordingly, the compounds are suitable especially for stimulating the body's own defence, for example in the case of cancer, chronic and acute infections or in the case of selective (antigen-specific) immunological defects, as well as in the case of general (that is to say not antigen-specific) immunological defective states that are either hereditary or acquired, such as arise in old age, in the course of severe primary diseases and, above all, after therapy with ionising rays or with pharmacological agents having an immunosuppressive action. The said compounds can also be administered in combination with antibiotics, chemotherapeutics or other substances in order to counteract immunological damage. Finally, the described compounds are also suitable for the general prophylaxis of infectious diseases in humans and animals.

In the acyl radicals $R_a{}^1CO$-, $R_b{}^1CO$- and $R^2CO$- of the compounds of the formula I and derivatives thereof and of the other compound groups given special mention above, especially the groups (IA) and (IB), $R_a{}^1$, $R_b{}^1$ and $R^2$ are saturated or unsaturated, aliphatic or cycloaliphatic-aliphatic hydrocarbon radicals having from 7 to 21 or (in the case of $R^2$) from 1 to 21 carbon atoms that are optionally also substituted by oxygen functions, that is to say the acyl radicals are derived from saturated or unsaturated, aliphatic or cycloaliphatic-aliphatic carboxylic acids that have from 8 to 22, or from 2 to 22, respectively, preferably from 8 to 16 or (in the case of $R^2$-CO) from 2 to 16, carbon atoms in the aliphatic moiety and that are optionally oxygenated in the hydrocarbon radical. As such there may be mentioned, for example, the saturated or unsaturated fatty acids having from 2 to 22 carbon atoms, especially having a straight, that is to say unbranched, carbon chain, such as acetic acid, propionic acid, oenanthic acid, butyric acid, caproic acid, caprylic acid, pelargonic acid, caproic acid, undecylic acid, lauric acid, myristic acid, palmitic acid, margaric acid, stearic acid, arachidic acid, behenic acid, oleic acid, elaidic acid, linoleic acid, α- and β-eleostearic acid, stearolic acid, α-linolenic acid, and also, of the cycloaliphatic-aliphatic acids of the type just mentioned in which the carbon chain is at any position substituted by a cycloalkyl or cycloalkenyl ring having preferably from 3 to 8 carbon atoms or interrupted by a cycloalkylene or cycloalkenylene radical having from 3 to 8 carbon atoms, for example dihydrosterculic acid, malvalic acid, hydnocarpic acid and chaulmoogric acid. Oxygenated acids of this type, which likewise come into consideration for the acyl radicals $R_a{}^1CO$-, $R_b{}^1CO$- and $R^2CO$-, are, for example, those resulting from epoxidation of the above-mentioned olefinic fatty acids and cycloaliphatic-aliphatic acids, for example δ,1-epoxystearic acid, and also derivatives of the above-mentioned acids that contain, for example, one or more hydroxy groups, such as, for example, ricinoleic acid.

Preferably, the radical $R^2$ has from 7 to 21 carbon atoms.

In the formula (I), the groups $R_a{}^1$, $R_b{}^1$ and $R^2$ may be identical to, or different from, one another.

Especially preferred are compounds according to formula (I) and derivatives thereof and the other compound groups given special mention, especially groups (IA) and (IB), in which $R_a{}^1$ and $R_b{}^1$ are different from $R^2$ especially those in which each of $R_a{}^1CO$-, $R_b{}^1CO$- and $R^2CO$-, independently of the others represents capryloyl, caprinoyl, lauroyl, myristoyl, palmitoyl or stearoyl.

A further preferred group of compounds according to the invention are the esters of the lipopeptides containing terminal and/or side chain carboxy groups and, of these, attention is drawn, in turn, to the esters of the sub-groups specified in more detail above, especially the compound groups (IA) and (IB). Such esters are derived especially from optionally substituted aliphatic, araliphatic, aromatic or heterocyclic alcohols, especially lower aliphatic alcohols having from 1 to 7 carbon atoms, such as methyl, ethyl, n-propyl or isopropyl alcohol or the butyl alcohols. Substituents are preferably free, esterified or etherified hydroxy groups, esterified groups preferably being derived from carboxylic acids having from 1 to 12 carbon atoms, preferably aliphatic carboxylic acids having from 1 to 7 carbon atoms, and etherified groups being derived from aliphatic alcohols having from 1 to 7 carbon atoms, and these groups being in any position, for example in the α-, β- or γ-position, to the alcohol function. Araliphatic alcohols are especially monocyclic-lower aliphatic alcohols having from 1 to 7 carbon atoms in the aliphatic moiety, such as, for example, benzyl alcohol. Aromatic esters are especially those of monocyclic, preferably substituted, phenols, for example p-lower alkoxyphenols, p-lower alkylaminophenols or dialkylaminophenols, lower alkyl again representing groups having from 1 to 7 carbon atoms, or p-halophenols, such as bromophenol, or, finally, phenol substituted by a $C_1$-$C_7$-alkyl group, for example, in the p-position. Heterocyclic alcohols are, for example, tetrahydrofuranol or tetrahydropyranol. Ester groups are thus, for example, acetoxy, propionyloxy, butyryloxy or pivaloyloxy, ether groups for example methoxy, ethoxy, propoxy or butoxy. There may be present in the alcohol component of the ester group one or more such substituents, that is to say the respective ester groups are derived, for example, from polyhydric alcohols or their semiesters or semiethers with the above-mentioned ester or ether groups, respectively. Thus, the esters may be derived especially from acyloxymethanols, such as, for example, from alkanoyloxymethyl alcohols having from 1 to 7 carbon atoms in the acyl group, for example pivaloyloxymethanol, propyleneglycol or glycerin, or $C_{3-8}$-cycloalkylcarbonyloxymethyl alcohols, or their mentioned semiesters or semiethers.

It is possible for all the carboxy groups of the peptide chain, or only some of them, to be in esterified form. Thus, depending on the nature of the substituents $Z^1$-$Z^3$ in formula I, it is posible to produce, for example, mono-, di-, -tri-, tetra-, penta-, hexa- (in the case where $Z^1=Z^2=Z^3=$Dpm-OAcyl) or nona-esters (in the case where $Z^1=Z^2=Z^3=$Dpm-Dpm-OAcyl). Preferably, compounds are produced in which in each case the α-carboxy group of the respective amino acid is esterified.

Of the amides of compounds according to formula (I), in which both the terminal and the side chain carboxy groups in the peptide chain may be in amidated form, attention is drawn in particular to the unsubstituted amides, it being possible also in this case to produce mono-, di-, tri-, tetra-, penta-, hexa- and nona-amides. As in the case of the esters, those amides are preferred in which in each case the α-carboxy group is amidated. Apart from the unsubstituted amides there come into consideration substituted amides that are derived especially from lower aliphatic, cyclic or acyclic, primary or secondary amines, especially from those in which the substituting alkyl radicals each contain from 1 to 7 carbon atoms or the substituting alkylene radical (in the case of cyclic bases) contains from 2 to 6 carbon atoms, such as, for example, methylamine, ethylamine, diethylamine, propylamine, isopropylamine, n-butylamine, or from pyrrolidine, piperidine or piperazine. Preferred are, again, the amides just mentioned from the specified compound groups, especially the groups (IA) and (IB).

The hydrocarbon radical Kw mentioned above in connection with the explanation of As° is a preferably unsubstituted alkylene radical having preferably from 2 to 6 carbon atoms, which is straight-chained or, especially, branched, such as an alkylidene radical, for example methylene, di-, tri- or tetramethylene and, especially, ethylidene, propylidene, 2,2-dimethylethylidene, butylidene, 3,3-dimethylpropylidene, 2-methylethylidene, 2-ethylethylidene and pentylidene. The radical -NH-Kw-CO in the case where Kw=alkylidene is the radical of α-amino acids, such as the natural amino acids glycine, alanine, α-aminobutyric acid, valine, norvaline, leucine, isoleucine and norleucine, but may also be derived from the corresponding compounds of the D-series, such as, for example, D-alanine. In the case where As° represents -O-Kw-CO-, such radicals are those of corresponding oxycarboxylic acids, especially of α-oxycarboxylic acids, for example the radical of glycolic acid and of lactic acid. In this case, too, radicals that are derived both from the L- and from the D-series may be present as radical As°, for example in radical of L- or D-lactic acid. Preferred are compounds of the above-specified compound groups, especially the groups (IA) and (IB), with the above-mentioned examples of the group As°.

The novel lipopeptides according to the present invention are characterised in that in the peptide sequence there follows the amino acid As¹ D-glutamic acid (D-Glu) or γ-carboxy-D-glutamic acid (D-Gla), or the amides thereof, such as the monoamides glutamine[Glu(NH₂)], isoglutamine[Glu-NH₂], Gla(NH₂) or Gla-NH₂ or the di- or tri-amides, for example Glu(NH₂)-NH₂ or Gla[(NH₂)₂]-NH₂.

The terminal side chain carboxy groups of these amino acids may especially be esterified or amidated or also linked by a peptide bond with other amino acids according to the definition of $Z^1$ and/or $Z^2$ or $Z^4$.

Preferred peptide sequences in componds of the formula (I) and derivatives thereof, and in the specified compound classes, especially the compound groups (IA) and (IB), are those in which n=O, that is to say those in which the compound member As° is missing from between the glycerylcysteine moiety and the amino acid As¹, and of these especially the sequences:

-Ala-D-Glu

-Ala-D-Glu-NH₂

-Ala-D-Glu(NH₂)

-Ala-D-Glu-D-Ala-NH₂

-Ala-D-Glu(NH₂)-NH₂

-Ala-D-Glu(Ala)-OH

-Ala-D-Glu(NH₂)-D-Ala-NH₂

-Ala-D-Glu(Ala)-NH₂ and corresponding sequences in which -Gly-, -Ser-, -Abu- or -Val- stand in place of the first alanine radical, and also corresponding sequences with a preceding As° which may be, for example, the radical of D- or L-alanine, D- or L-lactic acid, glycolic acid or glycine, or one of the radicals mentioned above for -NH-Kw-CO- or -O-Kw-CO-.

Of special interest are lipopeptides of the compound group (IB) having the R-configuration at the ** asymmetry centre, the radicals $R_a^1$-CO- and $R_b^1$-CO- having from 8 to 16 carbon atoms and radicals $R^2$-CO- having from 2 to 16 carbon atoms and with the preferred peptide chains indicated above. Preferably, the acyl radicals $R_a^1$-CO- and $R_b^1$-CO- are different from $R^2$-CO-, and $R_a^1$-CO-, $R_b^1$-CO- and $R^2$-CO- represent especially the radical of caprylic, capric, lauric, myristic, palmitic, stearic or oleic acid.

Especially important lipopeptides according to the Application are
palmitoyl-Cys(2[R],3-dilauroyloxy-propyl)-Ala-D-Glu-NH₂,
palmitoyl-Cys(2[R],3-dipalmitoyloxy-propyl)-Ala-D-Glu-(Ala)-NH₂,
palmitoyl-Cys(2[R],3-dilauroyloxy-propyl)-Ala-D-Glu(NH₂),
palmitoyl-Cys(2[R],3-dilauroyloxy-propyl)-Abu-D-Glu-NH₂,
palmitoyl-Cys(2[R],3-dilauroyloxy-propyl)-Ala-G-Glu-(NH₂)-OnBu,
palmitoyl-Cys(2[R],3-dilauroyloxy-propyl)-Ala-D-Glu-(OnBu)-NH₂,
palmitoyl-Cys(2[R],3-dilauroyloxy-propyl)-D-Ala-Ala-D-Glu-NH₂, palmitoyl-Cys(2[R],

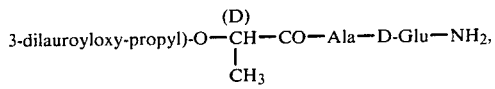

palmitoyl-Cys(2[R],3-dilauroyloxy-propyl)-O-CH₂CO-Ala-D-Glu-NH₂,
palmitoyl-Cys(2[R],3-dilauroyloxy-propyl)-Ala-D-Glu-(NH₂)-O-CH₂-O-CO-C(CH₃)₃,
palmitoyl-Cys(2[R],3-dilauroyloxy-propyl)-Ser-D-Glu-(OCH₃)-OCH₃,
palmitoyl-Cys(2[R],3-dilauroyloxy-propyl)-Ala-D-Glu-NH₂,
palmitoyl-Cys(2[R],3-dilauroyloxy-propyl)-Abu-D-Glu,
palmitoyl-Cys(2[R],3-dilauroyloxy-propyl)-Val-D-Glu-NH₂,
palmitoyl-Cys(2[R],3-dilauroyloxy-propyl)-αMeAla-D-Glu-NH₂,
palmitoyl-Cys(2[R],3-dilauroyloxy-propyl)-Ala-D-Glu-(Lys-OCH₃)-NH₂,
palmitoyl-Cys(2[R],3-dilauroyloxy-propyl)-Ala-D-Glu-(Lys-Lys-OCH₃)-NH₂,
palmitoyl-Cys(2[R],3-dilauroyloxy-propyl)-Ala-D-Glu-(Arg), the mono- and di-methyl ester and mono- and di-amide thereof, palmitoyl-Cys(2[R],

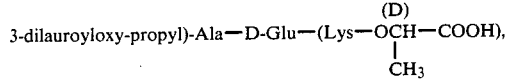

and mono- and di-methyl ester and the mono- and di-amide thereof,
palmitoyl-Cys(2[R],3-dilauroyloxy-propyl)-Ala-D-Glu(Tly), (Tly=4-thia-lysine), the mono- and di-methyl ester and the mono- and di-amide thereof, and corresponding lipopeptides in which, instead of palmitoyl there is present at the nitrogen of the cysteine radical lauroyl, caprinoyl, capryloyl or myristoyl, and compounds corresponding to these and to the above-listed lipopeptides in which there are present in the diacyloxypropyl radical instead of lauroyl radicals the radicals of palmitic, caprylic, capric and myristic acid, as well as the compounds corresponding to all of these lipopeptides in which the configuration at the chiral atom of the diacyloxypropyl radical is S instead of R, and corresponding diastereoisomeric mixtures of R and S compounds, such as, for example,
lauroyl-Cys(2[R,S],3-didecanoyloxy-propyl)-Ala-D-Glu-NH₂,
decanoyl-Cys(2[R,S],3-dilauroyloxy-propyl)-Ala-D-Glu-NH₂,
myristoyl-Cys(2[R,S],3-dilauroyloxy-propyl)-Ala-D-Glu-NH₂,
palmitoyl-Cys(2[R,S],3-didecanoyloxy-propyl)-Ala-D-Glu-NH₂,
palmitoyl-Cys(2[R,S],3-didecanoyloxy-propyl)-Abu-D-Glu(OCH₃)-OCH₃,
as well as, optionally, the unsubstituted amides thereof, the substituted amides thereof that are derived from lower aliphatic amines having $C_{1-7}$-alkyl radicals, especially from methylamine or ethylamine, or from pyrrolidine, piperidine or piperazine, and esters of aliphatic alcohols having from 1 to 7 carbon atoms, and also esters that are derived from substituted mono- and polyhydric alcohols, such as from $C_{1-7}$-alkanoyloxymethyl alcohols, $C_{1-7}$-alkanoyloxyethyl alcohols, ($C_{3-8}$-cycloalkyl)-carbonyloxymethyl alcohols or ($C_{3-8}$-cycloalkyl)-carbonyloxyethyl alcohols or from the above-mentioned substituted phenols. As specific esters of this type of lipopeptide according to the invention there may be mentioned, for example, the methyl, ethyl, butyl and propyleneglycol esters of the above-listed lipopeptides and of the specific lipopeptides described in the illustrative Examples. Of the lipopeptides according to the invention having an N-acyl radical $R^2$—CO— which is derived from a lower carboxylic acid, there may be mentioned, for example, acetyl-Cys(2[R],3-dilauroyloxy-propyl)-Ala-D-Glu-NH$_2$.

The invention relates especially to lipopeptides of the formula I in which each of $R_a{}^1$ and $R_b{}^1$, independently of the other, represents an aliphatic or cycloaliphatic-aliphatic hydrocarbon radical having from 7 to 21 carbon atoms that is unsubstituted or substituted by hydroxy or epoxy, or one of the radicals $R_a{}^1$-CO- and $R_b{}^1$-CO- represents hydrogen and the other of the radicals $R_a{}^1$-CO- and $R_b{}^1$-CO- represents an acyl radical, wherein $R_a{}^1$ and $R_b{}^1$ have the meanings given above, $R^2$ represents an aliphatic or cycloaliphatic-aliphatic hydrocarbon radical having from 1 to 21 carbon atoms that is unsubstituted or substituted by hydroxy or epoxy, n=0 or 1, As° represents a radical of the formula -O-Kw-CO- or -NH-Kw-CO- wherein Kw represents an aliphatic hydrocarbon radical having a maximum of 12 carbon atoms, As$^1$ represents an α-amino acid selected from glycine, alanine, α-methyl-alanine, N-methyl-alanine, serine, α-aminobutyric acid, valine or leucine, each of $Z^1$ and $Z^2$, independently of the other, represents hydroxy or the N-terminal radical of an α-aminocarboxylic acid selected from lysine, ornithine, α,α'-diamino-pimelic acid, glycine, D- and L-alanine, D-asparagine, lanthionine or arginine, of an ω-amino-$C_{2-3}$-alkanesulphonic acid or of a peptide having a maximum of 6 amino acids selected from lysine, ornithine, α,α'-diamino-pimelic acid, glycine, D- and L-alanine, D-asparagine, lanthionine, arginine and ω-amino-$C_{2-3}$-alkanesulphonic acids, and represents hydrogen or -CO-$Z^4$, wherein $Z^4$ represents hydroxy or the N-terminal radical of an α-amino acid selected from lysine, ornithine, α,α'-diamino-pimelic acid, glycine, D- and L-alanine, D-asparagine, lanthionine or arginine, of a ω-amino-$C_{2-3}$-alkanesulphonic acid or of a peptide having a maximum of 6 amino acids selected from lysine, ornithine, α,α'-diamino-pimelic acid, glycine, D- and L-alanine, D-asparagine, lanthionine, arginine and ω-amino-$C_{2-3}$-alkanesulphonic acids, and the amides and esters of such compounds that contain carboxy groups, wherein the centers of asymmetry designated by \*, \*\* and \*\*\* have the absolute configurations indicated, and the configuration at an asymmetric carbon atom carrying the group $Z^3$ may be R or S, and corresponding diastereoisomeric mixtures, as well as salts of such compounds having at least one salt-forming group and optionally complex salts of these compounds.

Preferred are lipopeptides of the formula I, wherein each of $R_a{}^1$, $R_b{}^1$ and $R^2$, independently of the other, represents an aliphatic hydrocarbon radical having from 7 to 21 carbon atoms or one of the radicals $R_a{}^1$-CO- and $R_b{}^1$-CO- represents hydrogen and the other of the radicals $R_a{}^1$-CO- and $R_b{}^1$-CO- represents an acyl radical, wherein $R_a{}^1$ and $R_b{}^1$ have the meanings given above, and $R^2$ has the meaning given above, n=0, As$^1$ represents an α-amino acid selected from the group consisting of Gly, Ala, Ser, Abu, Val, αMeAla and Leu, $Z^1$ represents hydroxy, the N-terminal radical of an amino acid selected from the group consisting of Lys, Orn, Dpm, Gly, Ala, D-Asn and D-Ala, an ω-amino-$C_{2-3}$-alkanesulphonic acid or a peptide consisting of 2 acids selected from the group consisting of Lys, Orn, Dpm, Gly, Ala, D-Asn, D-Ala and an ω-amino-$C_{2-3}$-alkanesulphonic acid, $Z^2$ represents hydroxy, the N-terminal radical of an amino acid selected from the group consisting of Lys, Orn, Dpm, Lan, Gly or Ala, an ω-amino-$C_{2-3}$-alkanesulphonic acid or a peptide consisting of 2 acids selected from the group consisting of Lys, Orn, Dpm, Lan, Gly, Ala or an ω-amino-$C_{2-3}$-alkanesulphonic acid, $Z^3$ represents hydrogen or -CO-$Z^4$, wherein $Z^4$ represents hydroxy or the N-terminal radical of an amino acid selected from the group consisting of Lys, Orn, Dpm, Lan, Gly or Ala, an ω-amino-$C_{2-3}$-alkanesulphonic acid or a peptide consisting of 2 acids selected from the group consisting of Lys, Orn, Dpm, Lan, Gly, Ala and an ω-amino-$C_{2-3}$-alkanesulphonic acid, and the esters of aliphatic alcohols having from 1 to 7 carbon atoms or the esters of $C_{1-7}$-alkanoyloxymethyl alcohols, $C_{1-7}$-alkanoyloxyethyl alcohols, ($C_{3-8}$-cycloalkyl)-carbonyloxymethyl alcohols, ($C_{3-8}$-cycloalkyl)-carbonyloxyethyl alcohols, propyleneglycol, glycerin, or of a $C_{1-7}$-alkoxy-, $C_{1-7}$-alkylamino-, di-($C_{1-7}$-alkyl)-amino or halophenol and unsubstituted amides or amides of $C_{1-7}$-alkylamines, pyrrolidine, piperidine or piperazine of such compounds that contain carboxy groups, as well as pharmaceutically acceptable salts of such compounds having at least one salt-forming group.

The invention relates more especially to lipopeptides of the formula I, in which the radicals $R_a{}^1$-CO-, $R_b{}^1$-CO- and $R^2$-CO-, independently of each other, are derived from caprylic, pelargonic, capric, undecylic, lauric, myristic, palmitic, margaric, stearic, arachidic, behenic, oleic, elaidic, linoleic, α- or β-eleostearic, stearolic or α-linolenic acid, n represents zero, As$^1$ represents an α-amino acid selected from glycine, alanine, α-methyl-alanine, N-methyl-alanine, serine, α-aminobutyric acid, valine or leucine, $Z^1$ represents amino, hydroxy or lower alkoxy, $Z^2$ represents the N-terminal radical of a dipeptide the N-terminal acid of which is selected from lysine, ornithine, α,α'-diamino-pimelic acid, glycine, D- and L-alanine, D-asparagine, lanthionine and arginine, and the remaining acid of which is selected from an ω-amino-$C_{2-3}$-alkanesulphonic acid, and $Z^3$ represents hydrogen, as well as pharmaceutically acceptable salts thereof.

The invention relates also to lipopeptides of the formula, wherein each of the radicals $R_a{}^1$-CO-, $R_b{}^1$-CO- and $R^2$-CO-, independently of the other, represents the acyl radical of caprylic acid, capric acid, lauric acid, myristic acid, palmitic acid, stearic acid or oleic acid, n represents 0, As$^1$ represents an α-amino acid selected from L-alanine, L-N-methyl-alanine, L-α-aminobutyric acid, L-valine or L-serine, $Z^1$ represents amino, hydroxy or lower alkoxy, $Z^2$ represents hydroxy, lower alkoxy, amino, the N-terminal radical of L-alanine, the N-terminal radical of L-alanine-benzylester the N-terminal radical of L-lysyl-L-lysine or or a lower alkyl ester thereof, the N-terminal radical of glycyl-taurine or of a pharmaceutically acceptable salt thereof, the N-terminal radical of L-arginine or of a lower alkyl ester thereof, or the N-terminal radical of L-lysyl-D-alanine, and $Z^3$ represents hydrogen, as well as pharmaceutically acceptable salts thereof. The invention relates especially to lipopeptides of the formula I wherein each of the radicals $R_a{}^1$-CO-, $R_b{}^1$-CO- and $R^2$-CO-, independently of the other, represents the acyl radical of caprylic acid, capric acid, lauric acid, myristic acid, palmitic acid, stearic acid or oleic acid, n represents 0, $As^1$ represents an α-amino acid selected from L-alanine, L-N-methyl-alanine, L-α-aminobutyric acid or L-valine, $Z^1$ represents amino or hydroxy, $Z^2$ represents hydroxy, the N-terminal radical of L-alanine, the N-terminal radical of the methylester of L-lysyl-L-lysine, the N-terminal radical of glycyl-taurine or of a pharmaceutically acceptable salt thereof, the N-terminal radical of the methylester of L-arginine or the N-terminal radical of L-lysyl-D-alanine, and $Z^3$ represents hydrogen, as well as pharmaceutically acceptable salts thereof.

Preferred are especially lipopeptides of the formula I, wherein each of the radicals $R_a{}^1$-CO-, $R_b{}^1$-CO- and $R^2$-CO-, independently of the other, represents the acyl radical of caprylic acid, capric acid, palmitic acid, stearic acid or oleic acid, n represents 0, $As^1$ represents an α-amino acid selected from L-alanine, L-N-methyl-alanine, L-α-aminobutyric acid or L-valine, $Z^1$ represents amino or hydroxy, $Z^2$ represents the N-terminal radical of a dipeptide, the N-terminal acid of which is selected from glycine and L-alanine and the remaining acid of which is a ω-amino-$C_{2-3}$-alkanesulphonic acid, and $Z^3$ represents hydrogen, as well as pharmaceutically acceptable salts thereof.

The invention relates first and foremost to the compounds of the formula I mentioned in the Examples.

Depending on the nature of their substituents, the present novel lipopeptides are neutral, acidic or basic compounds. If excess acidic groups are present, they form salts with bases, such as ammonium salts, or salts with alkali metals or alkaline metals, for example, sodium, potassium, calcium or magnesium; if, however, excess basic groups are present, they form acid addition salts.

Acid addition salts are especially pharmaceutically acceptable, non-toxic acid addition salts, such as those with inorganic acids, for example hydrochloric acid, hydrobromic acid, nitric acid, sulphuric acid or phosphoric acid, or with organic acids, such as organic carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 4-phenoxybenzoic acid, 2-acetoxybenzoic acid, embonic acid, nicotinic acid or isonicotinic acid, or organic sulphonic acids, for example methanesulphonic acid, ethanesulphonic acid, 2-hydroxyethanesulphonic acid, ethane-1,2-disulphonic acid, benzenesulphonic acid, p-toluenesulphonic acid or naphthalene-2-sulphonic acid, and also other acid addition salts which can be used, for example, as intermediates, for example for purification of the free compounds, or in the preparation of other salts, as well as for characterisation, such as, for example, those with picric acid, picrolonic acid, flavianic acid, phosphotungstic acid, phosphomolybdic acid, chloroplatinic acid, Reinecke's acid or perchloric acid.

Complex salts are the compounds formed with metal salts, for example with heavy metal salts, such as copper, zinc, iron or cobalt salts. To form such complexes there are preferably used the phosphates, pyrophosphates and polyphosphates of these metals, optionally in combination with acidic organic substances, for example polysaccharides containing acidic groups, such as carboxymethylcellulose, tannic acid, polyglutamic acid or partially hydrolysed gelatin, also alkali metal polyphosphates, such as, for example, "Calgon N", "Calgon 322", "Calgon 188" or "Plyron B 12".

The novel lipopeptides can be produced by methods known per se. According to a preferred process, the compounds of the formula (I), the amides and/or esters thereof or the diastereoisomeric mixtures thereof and the salts and complex salts thereof are produced as follows:

(a) in a compound corresponding to the formula (I) or in a salt thereof, in which the substituents have the meanings given above with the proviso that the peptide chain

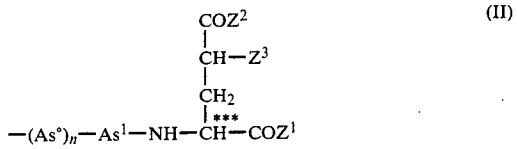

contains at least one protected functional group, the protecting group(s) is (are) removed, or (b) a compound of the formula I in which at least one of the radicals $R_a{}^1$-CO-, $R_b{}^1$-CO- and $R^2$-CO- represents hydrogen and the remaining substituents have the meanings given above with the proviso that any free functional groups present in this starting material, with the exception of the hydroxy and/or amino group(s) participating in the reaction, are, if necessary, in protected form, or a salt thereof, is acylated with an acid $R_a{}^1$-COOH, $R_b{}^1$-COOH or $R^2$-COOH or a reactive carboxylic acid derivative thereof, and any protecting groups present are removed, or (c) an amide bond of a compound of the formula I is produced by reacting a corresponding fragment of a compound of the formula I having a free carboxy group, or a reactive acid derivative thereof, with a complementary fragment having a free amino group or with a reactive derivative thereof having an activated amino group, any free functional groups present in the reactants, with the exceptional of the groups participating in the reaction, if necessary being in protected form, and any protecting groups present are removed, or (d) in a compound of the formula (I) in which at least one free carboxy group is present, the free carboxy group(s) is (are) esterified or amidated and/or, in a compound of the formula (I) in which at least one ester group is present, the ester group(s) is (are) hydrolysed, or (e) a compound of the formula III

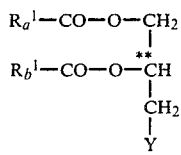

$$R_a^1-CO-O-CH_2 \quad (III)$$
$$R_b^1-CO-O-\overset{**}{C}H$$
$$\phantom{R_b^1-CO-O-}CH_2$$
$$\phantom{R_b^1-CO-O-}Y$$

** = R or S in which $R_a^1$ and $R_b^1$ have the meanings given above and Y represents a nucleofugal group is reacted with a compound of the formula IV

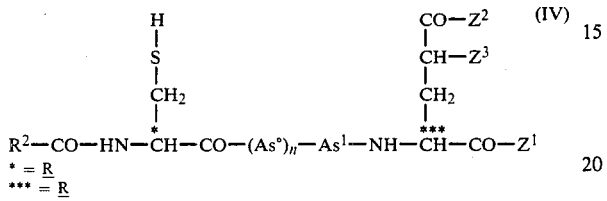

in which the substituents have the meanings given above, wherein free functional groups, with the exception of the mercapto group participating in the reaction, are if necessary protected by readily removable protecting groups, or with a reactive derivative of a compound of the formula IV, and any protecting groups present are removed, or (f) a compound of the formula V

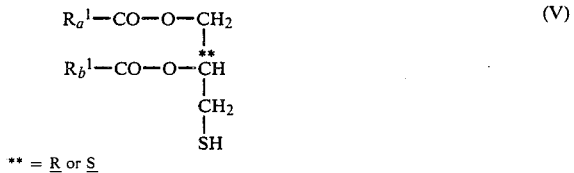

** = R or S in which $R_a^1$ and $R_b^1$ have the meanings given above, or a reactive derivative of this compound, is reacted with a compound of the formula VI

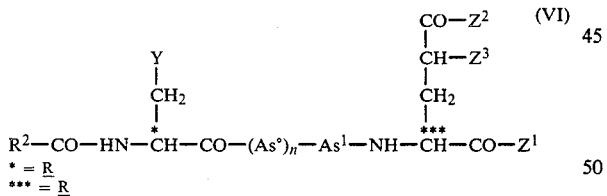

in which Y represents a nucleofugal group and the remaining substituents have the meanings given above, wherein free functional groups are, if necessary, in protected form, and any protecting groups present are removed, and, if desired, after carrying out one of the process variants (a–f), a resulting compound of the formula I having at least one salt-forming group is converted into a salt or complex salt, or a resulting salt or complex salt is converted into the free compound and, if desired, resulting mixtures of isomers are resolved.

Process (a):

The protecting groups in the starting materials for the process according to variant (a) are especially those known from the synthesis of peptides for the protection of amino, carboxy or hydroxy groups, which can be removed, for example, by hydrolysis, reduction, aminolysis or hydrazinolysis.

Thus, for example, protecting groups for amino groups are acyl or aralkyl groups, such as formyl, trifluoroaccetyl, phthaloyl, benzenesulphonyl, p-toluenesulphonyl, o-nitrophenylsulphenyl and 2,4-dinitrophenylsulphenyl groups; benzyl or diphenyl- or triphenyl-methyl groups that are optionally substituted, for example, by lower alkoxy groups, especially by o- or p-methoxy groups; or groups derived from carbonic acid, such as arylmethoxycarbonyl groups that are optionally substituted in the aromatic rings, for example by halogen atoms, such as chlorine or bromine, nitro groups, lower alkyl or lower alkoxy groups or by chromophoric groups, for example azo groups, and in which the methylene group can be substituted by a further aryl radical and/or by one or optionally two lower alkyl radicals, such as benzyloxycarbonyl, benzhydryloxycarbonyl or 2-phenylisopropyloxycarbonyl groups, for example benzyloxycarbonyl, p-bromo- or p-chlorobenzyloxycarbonyl, p-nitrobenzyloxycarbonyl or p-methoxybenzyloxycarbonyl, p-phenylazobenzyloxycarbonyl and p-(p'-methoxyphenylazo)-benzyloxycarbonyl, 2-tolylisopropoxycarbonyl and, especially, 2-(p-biphenylyl)-isopropoxycarbonyl, as well as aliphatic oxycarbonyl groups, such as adamantyloxycarbonyl, cyclopentyloxycarbonyl, trichloroethoxycarbonyl, tert.-amyloxycarbonyl or, above all, tert.-butoxycarbonyl.

The amino groups can also be protected by the formation of enamines, obtained by reaction of the amino group with 1,3-diketones, for example benzoylacetone, acetylacetone or dimedone.

Carboxy groups are protected, for example, by amide or hydrazide formation or by esterification. The amide or hydrazide groups are preferably substituted: the amide group, for example, by the 3,4-dimethoxybenzyl- or bis-(p-methoxyphenyl)-methyl group; the hydrazide group, for example, by the benzyloxycarbonyl group, the trichloroethoxycarbonyl group, the trifluoroacetyl group, the trityl group, the tert.-butoxycarbonyl group or the 2-(p-biphenylyl)-isopropoxycarbonyl group. Suitable for esterification are, for example, lower optionally substituted alkanols, such as methanol, ethanol, cyanomethyl alcohol, benzoylmethyl alcohol or, especially, tert.-butanol, also aralkanols, such as aryl-lower alkanols, for example benzyl alcohols or benzhydrols optionally substituted by lower alkyl or lower alkoxy groups or halogen atoms, such as benzhydrol, p-nitrobenzyl alcohol, p-methoxybenzyl alcohol, 2,4,6-trimethylbenzyl alcohol; phenols and thiophenols optionally substituted by electron-attracting substituents, such as thiophenol, thiocresol, p-nitrothiophenol, 2,4,5- and 2,4,6-trichlorophenol, p-cyanophenol or p-methanesulphonylphenol; and also, for example, N-hydroxysuccinimide, N-hydroxyphthalimide, N-hydroxypiperidine and 8-hydroxyquinoline.

Hydroxy groups, for example in serine and threonine radicals, can be protected, for example, by esterification or etherification.

Suitable acyl radicals for the esterification are, above all, radicals derived from carbonic acid, such as benzyloxycarbonyl or ethoxycarbonyl. Groups suitable for etherification are, for example, benzyl, tetrahydropyranyl or tert.-butyl radicals. Suitable for protecting the hydroxy groups are also the 2,2,2-trifluoro-1-tert.-butoxycarbonylaminoethyl or 2,2,2-trifluoro-1-benzyloxycarbonylaminoethyl groups (Weygand) described in Chem. Ber. 100 (1967), 3838–3849.

Special protecting groups for carboxy groups, which can be removed under neutral conditions, are the hydrocarbyl-silyl-ethyl groups described in German Offenlegungsschrift No. 27 06 490, such as, for example, the 2-(trimethylsilyl)-ethyl group.

A mercapto group, such as, for example, in cysteine, may be protected especially by S-alkylation with optionally substituted alkyl radicals, thioacetal formation, S-acylation or by the establishment of asymmetric disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl moiety, for example by methoxy, such as 4,4'-dimethoxydiphenylmethyl, triphenylmethyl, trimethylsilyl, benzylthiomethyl, tetrahydropyranyl, acylaminomethyl, benzoyl, benzyloxycarbonyl or aminocarbonyl, such as ethylaminocarbonyl.

The removal of the protecting groups in accordance with the process is carried out in a manner known per se, for example according to methods customary in peptide chemistry. For example, the above-mentioned amino-protecting groups, such as acyl protecting groups, can be removed by acidic hydrolysis, for example with trifluoroacetic acid, hydrogen chloride or hydrogen bromide, in a suitable solvent, such as an ester, for example ethyl acetate, or a chlorinated aliphatic hydrocarbon, such as chloroform, methylene chloride or ethylene chloride. In the case of sulphenyl groups, removal can also be effected by the action of nucleophilic reagents, for example sulphites or thiosulphites. Aralkyl groups are preferably removed by catalytic hydrogenation, for example with palladium catalysts, such as palladium/barium sulphate, palladium/Mohr or alternatively with a rhodium catalyst, using solvents known from the literature, for example cyclic ethers, such as tetrahydrofuran, optionally in admixture with other inert solvents, such as, for example, a lower aliphatic acid amide, such as dimethylformamide.

The removal of carboxy-protecting groups can also be carried out by hydrolysis (under the indicated neutral or mild acidic conditions), for example with the same acidic agents as those mentioned above for removing amino-protecting groups. Aralkyl esters, such as, for example, benzyl esters can, however, also be removed by catalytic hydrogenation, such as in the case of the above-mentioned 2-(trimethylsilyl)-ethyl group can be removed under neutral conditions, for example by the action of a salt of hydrofluoric acid, such as especially the hydrofluoric acid salt of a quaternary nitrogen base, for example tetraethylammonium fluoride, in a suitable solvent.

A hydroxy or mercapto group protected by a suitable acyl group, an organic silyl group by optionally substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group etherified by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are together protected by means of a preferably substituted methylene group, such as by lower alkylidene, for example isopropylidene, cycloalkylidene, for example cyclohexylidene, or benzylidene, can be freed by acidic solvolysis, especially in the presence of a mineral acid or a strong organic acid.

In the starting materials according to variant (a), carboxy groups protected by esterification are especially tert.-butoxycarbonyl or benzyloxycarbonyl groups.

Amino groups of side chains, such as of ornithine or lysine, are protected especially by the tert.-butoxycarbonyl group (Boc). Hydroxy groups, for example in serine in $As^1$, are protected above all by the tert.-butyl ether group. The removal of these group is carried out advantageously by treatment with the mentioned acidic agents under the known conditions, for example with trifluoroacetic acid, at room temperature, so that the protecting groups both of the carboxy groups and of the amino groups and in certain cases of serine can be removed in one step.

Process (b):

Free functional groups in the starting material, which are preferably in protected form if they are not to participate in the reaction, are especially amino, mercapto, hydroxy and carboxy groups. The esterification with the free carboxylic acid is carried out in the presence of a suitable water-removing agent. Reactive carboxylic acid derivatives are especially the anhydrides, such as, for example, mixed or internal anhydrides, for example those with hydrohalic acids, that is to say the corresponding acid halides, especially chlorides, and those with hydrocyanic acid or those with suitable carbonic acid semi-derivatives, such as corresponding semi-esters (such as the mixed anhydrides formed, for example, with a haloformic acid lower alkyl, such as chloroformic acid ethyl ester or isobutyl ester) or with lower alkanecarboxylic acids optionally substituted, for example, by halogen, such as chlorine (such as the mixed anhydrides formed with pivalic acid chloride or trichloroacetic acid chloride). Internal anhydrides are, for example, those of organic carboxylic acids, that is to say ketenes, such as ketene or diketene, or those of carbamic or thiocarbamic acids, that is to say isocyanates or isothiocyanates. Other reactive derivatives of organic carboxylic acids that can be used as acylating agents are activated esters, such as suitably substituted lower alkyl esters, for example cyanomethyl ester, or suitably substituted phenyl esters, for example pentachlorophenyl or 4-nitrophenyl ester. The esterification can, if necessary, be carried out in the presence of suitable condensation agents, when using free carboxylic acids for example in the presence of carbodiimide compounds, such as dicyclohexyl carbodiimide, or carbonyl compounds, such as diimidazolylcarbonyl, and when using reactive acid derivatives for example in the presence of basic agents, such as trilower alkylamines, for example triethylamine, or heterocyclic bases, for example pyridine or 4-dimethylaminopyridine. The acylation reaction can be carried out in the absence or presence of a solvent or solvent mixture, while cooling, at room temperature or while heating and, if necessary, in a closed vessel and/or in an inert gas atmosphere, for example a nitrogenatmosphere. Suitable solvents are, for example, optionally substituted, especially optionally chlorinated, aliphatic, cycloaliphatic or aromatic hydrocarbons, such as benzene or toluene, it being possible to use suitable esterifying reagents, such as acetic anhydride, also as diluents.

Protecting groups are, for example, those mentioned for process (a).

Process (c):

A fragment of a compoundd of the formula I having a free carboxy group is, for example, a carboxylic acid of the formula VII, VIII, IX, X or XI,

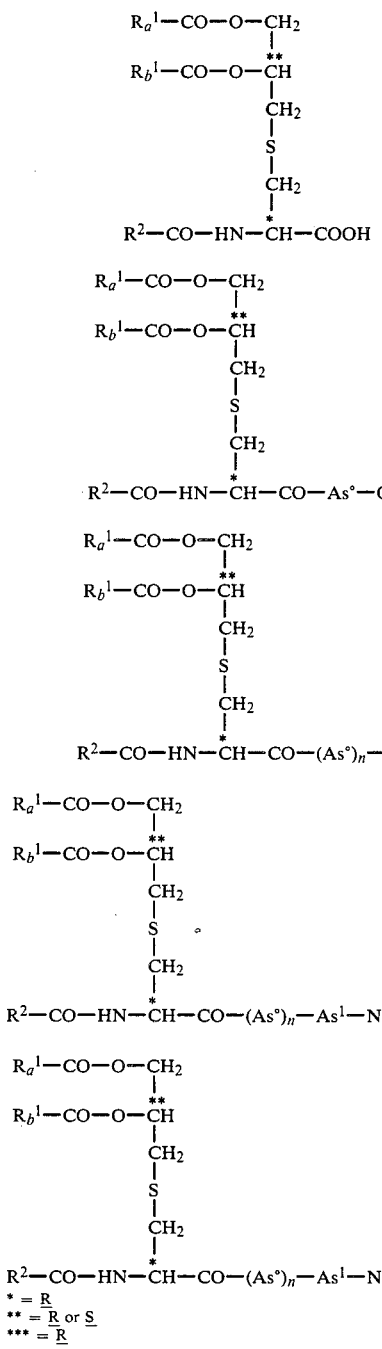

```
* = R
** = R or S
*** = R
``` in which the substituents have the meanings given above, wherein free functional groups, with the exception of the carboxy group participating in the reaction, are, if necessary, in protected form. Functional groups in such a fragment, which are preferably in protected form, are especially amino groups or other carboxy groups, and apart from these, for example, also hydroxy or mercapto groups. A complementary fragment having a free amino group is, for example, in the case of a carboxylic acid of the formula VII an amino compound of the formula XII, in the case of a carboxylic acid of the formula VIII an amino compound of the formula XIII, in the case of a carboxylic acid of the formula IX an amino compound of the formula XIV, in the case of a carboxylic acid of the formula X an amino compound of the formula XV, and in the case of a carboxylic acid of the formula XI an amino compound of the formula XVI,

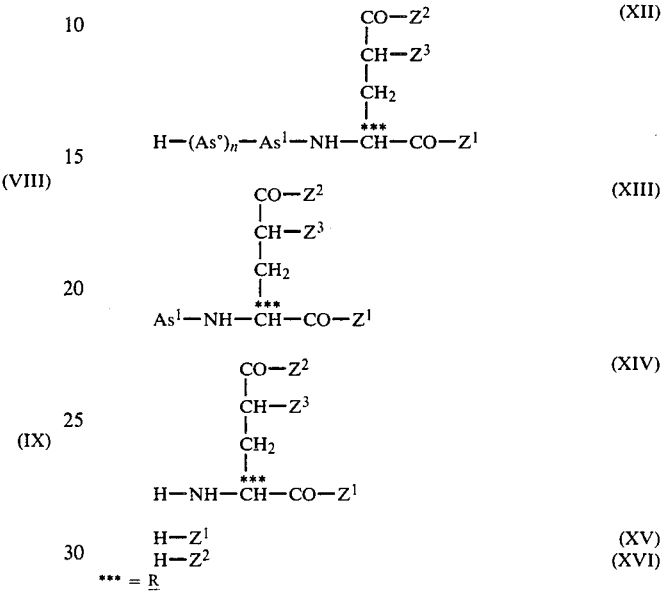

```
*** = R
``` in which the substituents in the formulae XII, XIII, XIV, XV and XVI have the meanings given above, with the proviso that free functional groups present in the compounds of the formulae XII to XVI, with the exception of the amino group participating in the reaction, are, if necessary, in protected form.

Functional groups in such a complementary fragment, which are preferably in protected form, are above all carboxy groups or other amino groups, and apart from these, for example, also hydroxy or mercapto groups.

A preferred embodiment of process variant (c) is the reaction of a reactive acid derivative with the complementary fragment having a free amino group, it being possible for the activation of the acid also to be effected in situ. In addition, it is also possible to react the acid with a complementary fragment of which the amino group is in activated form.

A reactive acid derivative is, for example, an acid azide, anhydride, imidazolide or isoxazolide or an activated ester, such as cyanomethyl ester, carboxymethyl ester, thiophenyl ester, p-nitrothiophenyl ester, thiocresyl ester, p-methanesulphonylphenyl ester, p-nitrophenyl ester, 2,4-dinitrophenyl ester, 2,4,5- or 2,4,6-trichlorophenyl ester, pentachlorophenyl ester, an ester with N-hydroxysuccininimide, N-hydroxyphthalimide, 8-hydroxyquinoline, 2-hydroxy-1,2-dihydro-1-ethoxycarbonylquinoline or N-hydroxypiperidine, or is an enol ester that is obtained with N-ethyl-5-phenylisoxazolium 3-sulphonate [Woodward reagent], or can be formed, optionally in situ, by reaction of the acid with a carbodiimide (optionally with the addition of N-hydroxysuccinimide) or with an unsubstituted or, for example, halogen-, methyl- or methoxy-substituted, 1-hydroxybenzotriazole, 3-hydroxy-4-oxo-3,4-dihydrobenzo[d]-1,2,3-triazine or N,N'-carbonyldiimidazole.

A reactive derivative having an activated amino group can be formed, for example, by reaction of the amino compound with a phosphite.

The following may be mentioned as the most customary methods of condensation: the method according to Weygand-Wünsch (carbodiimide in the presence of N-hydroxysuccinimide), the azide method, the N-carboxyanhydride or N-thiocarboxyanhydride method, the activated ester method and the anhydride method. These condensation reactions can especially also be accomplished according to the Merrifield method.

Process (d):

In accordance with process variant (d), the terminal carboxy groups of the amino acid sequence of compounds of the formula (I) can be amidated or esterified. These reactions are carried out in a conventional manner known per se. Thus, amides can be produced, for example, by reaction of carboxylic acids with ammonia or an amine or by reaction of a reactive derivative of the carboxylic acid, such as an acid halide or acid ester, with the said reagents. In particular, the amidation methods customary in peptide chemistry are used, for example reaction of an activated carboxylic acid derivative with the desired amide or with ammonia in accordance with the methods discussed above for process variant (c). The esterification is carried out, for example, according to methods known per se. For example, the free acid is reacted with a reactive functional derivative of the respective alcohol, such as an alkyl halide, for example an alkyl bromide or chloride, or a dialkyl sulphate, such as dimethyl sulphate, in the presence of a base, such as pyridine or sodium bicarbonate, or the reaction is carried out directly with the alcohol with the addition of a suitable dehydrating agent. The acids can also be reacted in a manner known per se with a diazoalkane, for example diazomethane, preferably in an ether and at temperatures between $-5°$ and $+30°$, or with the respective O-alkyl-N',N-dicyclohexylisothiourea, preferably in an aprotic medium and at temperatures between $25°$ and $100°$. It can, however, be very advantageous also to use metal salts of carboxylic acids, especially alkali metal salts, as starting materials, and to react these with the halogenated hydrocarbon corresponding to the ester to be produced: there is used, for example, an alkyl halide, such as methyl bromide, ethyl chloride or benzyl chloride, or a dialkyl sulphate, such as dimethyl sulphate, and the reaction is carried out preferably in a polar solvent, such as, for example, acetone, methyl ethyl ketone or dimethylformamide, preferably at temperatures between $25°$ and $100°$. There are used as metal salts preferably those of sodium or potassium or especially also those of caesium. Instead of the mentioned alkyl halides there may advantageously be used also their addition products with tertiary amines, that is to say quaternary tetraalkylammonium salts.

Finally, the esters can also be produced from functional derivatives of carboxylic acids, for example optionally from the halides thereof, by reaction with the desired alcohol, or from other esters by transesterification.

The conversion of ester groups into carboxylic acid groups to be undertaken in accordance with process variant (d) is likewise effected according to methods known per se.

For the hydrolysis, hydrolytic processes with acidic or basic agents or optionally reductive methods can be used: for example benzyl esters can be cleaved to form the carboxylic acid by catalytic reduction in a manner known per se, for example with palladium catalysts.

Process (e):

A nucleofugal group Y is a leaving group in a nucleophilic substitution, for example a preferably esterified hydroxy group, the hydroxy group being esterified especially by strong inorganic or organic acids, for example mineral or sulphonic acids. A nucleofugal group Y is thus, for example, chloride, bromide, iodide, mono- or di-alkyl sulphate or toluenesulphonate.

Functional groups in a compound of the formula IV, which are preferably protected by readily removable protecting groups, are above all other mercapto groups, but also hydroxy, amino or carboxy groups. A reactive derivative of a compound of the formula IV is a compound in which the nucleophilicity of the sulphur atom participating in the reaction is increased, for example by removal of the proton of the mercapto group. Such a reactive derivative can optionally also be formed in situ.

The reaction can be carried out, for example, analogously to that described in European Patent Specification No. 0 000 330 or in K. H. Wiesmüller, W. Bessler and G. Jung, Hoppe-Seyler's Z. Physiol. Chem. 364, 593–606 (1983).

Process (f):

A reactive derivative of a compound of the formula V is a compound in which the nucleophilicity of the sulphur atom participating in the reaction is increased, for example by removal of the proton of the mercapto group. Such a reactive derivative can optionally also be formed in situ.

A nucleofugal group Y is, for example, one of the groups mentioned in process (e).

Functional groups in a compound of the formula VI, which are preferably in protected form, are above all mercapto, but apart from that also hydroxy, amino and carboxy groups.

Unless specified to the contrary hereinbefore, processes (a) to (f) are carried out in an inert solvent or solvent mixture at a temperature between approximately $-20°$ C. and approximately $+120°$ C. and, if necessary, under a protecting gas.

The starting materials for the above-described processes according to the present invention are known, for example from European Patent Specification No. 0 000 330, or can be produced in a manner known per se, for example analogously to the abovementioned processes.

Starting materials in which the radical $R^2$-CO- in formula I represents hydrogen can be obtained, for example, by reaction of the glycerylcysteine, which is protected at the amino group by a readily removable protecting group and contains a carboxy group present in activated form, with the desired peptide in accordance with the same process as for process variant (c), with subsequent removal of the amino-protecting group. Alternatively, S-(2,3-dihydroxypropyl)-cysteine provided at the amino group with a readily removable protecting group can first of all be acylated, then condensed with the peptide, and subsequently the amino-protecting group can be removed. The removal can advantageously be effected in slightly acidic or neutral medium.

The starting materials for process (a) can be obtained by the same methods as for process (c) with the difference that at least one of the functional groups in the amino acids, that is to say the amino, carboxy or hydroxy group, is in protected form.

The peptides according to formula (XII) or their fragments can be produced according to methods known in peptide chemistry, especially according to those mentioned above for process (c). The building blocks thereof, especially also D-glutamic acid or D-γ-carboxyglutamic acid and their amides, are known compounds. The N-acyl-glyceryl-cysteines or the derivatives thereof also acylated in the glycerine moiety used as starting materials are derivatives of natural L-cysteine (configuration R). Mixtures of diastereoisomers can, if desired, be resolved into the individual diastereoisomers in a manner known per se.

Terminal or side chain carboxy groups can, at any stage of these manufacturing processes for the starting materials, be modified in the desired manner, for example esterified or amidated, according to methods known per se.

The lipopeptides obtained can be converted into their salts in a manner known per se, for example by reacting resulting acidic compounds with alkali hydroxides or alkaline earth hydroxides, or by reacting resulting basic compounds with acids. The salts can be brought from their solutions into a form suitable for pharmaceutical use, for example by lyophilisation.

Owing to the close relationship between the novel compounds in the free form and in the form of their salts and complex salts, hereinbefore and hereinafter there may be inserted, or used instead of the free compounds, where appropriate and expedient optionally also the corresponding salts.

Resulting isomeric mixtures can be separated in known manner on the basis of the physical-chemical differences between their constituents, for example by chromatography and/or by fractional crystallisation. Advantageously, the more active of the isomers is isolated.

The processes described above are carried out, for example, by methods known per se, in the absence or preferably in the presence of diluents or solvents, if necessary with cooling or heating, under elevated pressure and/or in an inert gas atmosphere, such as a nitrogen atmosphere. With due regard being given to all substituents present in the molecule, there are to be used if necessary, especially where readily hydrolysable O-acyl radicals are present, especially gentle reaction conditions, such as short reaction times, mild acidic agents at low concentration, stoichiometric quantity ratios, and suitable catalysts, solvents, temperature and/or pressure conditions.

The invention relates also to those embodiments of the process in which a compound obtainable as an intermediate at any stage of the process is used as starting material and the remaining process steps are carried out, or in which the process is discontinued at any stage, or a starting material is formed under the reaction conditions or is used in the form of a reactive derivative or salt. There are preferably used those starting materials which, according to the process, yield the compounds described in the foregoing as being especially valuable.

The present invention relates also to pharmaceutical preparations that contain the described novel lipopeptides according to the invention, their mixtures, salts or complex salts. The pharmaceutical preparations according to the invention are preparations for enteral administration, such as oral or rectal administration, and especially parenteral or topical, for example nasal or vaginal, administration, to warm-blooded animals, which contain the pharmacological active ingredient alone or together with a pharmaceutically acceptable carrier. The dosage of active ingredient depends on the species, the age and the individual condition of the warm-blooded animal concerned, and also on the mode of administration. Thus, for example, to achieve an immunity-potentiating effect in warm-blooded animals having a low body weight, for example mice, in the case of subcutaneous administration doses in the range of approximately 1–30 mg/kg body weight are administered and, in the case of intraperitoneal administration, doses in the range of 0.03–3 mg/kg body weight are administered. Owing to the weakly pronounced relationship between dosage and effect, the dosage for warm-blooded animals having a higher body weight, for example humans with a body weight of approximately 70 kg, is from 0.01 to approximately 5 mg per human. Depending on the illness to be treated, this dosage is administered, for example subcutaneously, either only once during the duration of the illness or approximately twice per week over a period of approximately 4 weeks.

The oral and rectal forms of the novel pharmaceutical preparations contain from approximately 1% to approximately 95%, preferably from approximately 10% to approximately 95%, especially from approximately 20% to approximately 90%, of active ingredient: they may, for example, be in unit dose form, such as in the form of dragées, tablets, capsules, suppositories or ampoules, and can be produced in a manner known per se, for example by means of conventional mixing, granulating, confectioning, dissolving or lyophilising processes.

Suitable carriers for the oral forms are especially fillers, such as sugars, for example lactose, saccharose, mannitol or sorbitol, cellulose preparations and/or calcium phosphates, for example tricalcium phosphate or calcium hydrogen phosphate; also binders, such as starch pastes, using, for example, maize starch, wheat starch, rich starch or potato starch, gelatin, tragacanth, methylcellulose, hydroxypropylmethylcellulose, sodium carboxymethylcellulose and/or polyvinylpyrrolidone, and/or, if desired, disintegrating agents, such as the aforementioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings that are optionally resistant to gastric juices, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures, or, for the production of coatings that are resistant to gastric juices, solutions of suitable cellulose preparations, such as microcrystalline cellulose (Avicel), acetylcellulose phthalate or hydroxypropylmethylcellulose phthalate. Dyes or pigments can be added to the tablets or dragée coatings, for example for identication purposes or to indicate different doses of active ingredient.

Further pharmaceutical preparations for oral administration are dry-filled capsules consisting of gelatin and also soft, sealed capsules consisting of gelatin and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

There are suitable for parenteral administration especially aqueous solutions of an active ingredient in water-soluble form, for example a water-soluble salt, also suspensions of the active ingredient, such as corresponding oily injection suspensions, using suitable lipophilic solvents or vehicles, such as fatty oils, for example sesame oil, or synthetic fatty acid esters, for example ethyl oleate or triglycerides, or aqueous injection suspensions containing substances that increase the viscosity, for example sodium carboxymethylcellulose, sorbitol and/or dextran, and, optionally, also stabilisers.

The pharmaceutical preparations for parenteral use contain preferably between 0.1% and 75%, especially between 1% and 50%, of active ingredient.

There come into consideration as preparations for topical use, for example, creams, ointments, pastes, foams, tinctures and solutions that preferably contain from approximately 0.02% to approximately 2% of active ingredient.

Creams are oil-in-water emulsions that contain more than 50% of water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. As emulsifiers there come into consideration surface-active substances having predominantly hydrophilic properties, such as correspondingly non-ionic emulsifiers, for example fatty acid esters of polyalcohols, or ethylene oxide adducts thereof, such as polyglycerine fatty acid esters or polyoxyethylene sorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the aqueous phase are, inter alia, agents that reduce the drying out of the creams, for example polyalcohols, such as glycerine, sorbitol, propylene glycol and/or polyethylene glycols, and also preservatives, perfumes etc..

Ointments are water-in-oil emulsions that contain up to 70%, but preferably from approximately 20% to approximately 50%, of water or aqueous phase. As fatty phase there come into consideration especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives, perfumes etc..

Fatty ointments are anhydrous and contain as base especially hydrocarbons, for example paraffin, petroleum jelly and/or liquid paraffins, and also natural or partially synthetic fats, for example coconut fatty acid triglyceride, or preferably hardened oils, for example hydrogenated ground nut oil or castor oil, and also fatty acid partial esters or glycerine, for example glycerine mono- and di-stearate, and also, for example, the fatty alcohols, which increase the water-absorbing capacity, emulsifiers and/or additives mentioned in connection with the ointments.

Pastes are creams and ointments containing powder ingredients that absorb secretions, such as metal oxides, for titanium oxide or zinc oxide, also talc and/or aluminium silicates, the purpose of which is to bind any moisture or secretions present.

Foams are administered from pressurised containers and are liquid oil-in-water emulsions in aerosol form, halogenated hydrocarbons, such as chlorofluoro-lower alkanes, for example dichlorodifluoromethane and dichlorotetrafluoroethane, being used as propellants. For the oily phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers having predominantly hydrophilic properties, such as polyoxyethylene sorbitan fatty acid esters (Tweens), and those having predominantly lipophilic properties, such as sorbitan fatty acid esters (Spans). In addition, there may be used customary additives, such as preservatives etc..

Tinctures and solutions generally have an aqueous ethanolic base to which there are added, inter alia, polyalcohols, for example glycerine, glycols, and/or polyethylene glycol, as humectants for reducing evaporation, and fat-restoring substances, such as fatty acid esters with lower polyethylene glycols, that is to say lipophilic substance that are soluble in the aqueous mixture, to replace the fatty substances that are removed from the skin by the ethanol, and, if necessary, other adjuncts and additives.

The pharmaceutical preparations for topical use are manufactured in a manner known per se, for example by dissolving or suspending the active ingredient in the base or, if necessary, in a part thereof. When processing the active ingredient in the form of a solution, it is usually dissolve in one of the two phases before emulsification; when processing the active ingredient in the form of a suspension, it is mixed with a part of the base after emulsification and then added to the remainder of the formulation.

Especially advantageous is the use of pharmaceutical preparations in liposome form. The lipopeptide is added during the formation of the liposomes. The manufacture of liposomes and the inclusion of the active ingredient can be carried out in various ways and is described in the review article of Kaye, St. B., Cancer Treatment Reviews (1981) 8, 27–50. Other processes for the manufacture of liposomes as carriers of active ingredients are described also by Barenholz et al. in Biochemistry, Vol. 16, No. 12, 2806–2810, and in the German Offenlegungsschriften (DOS) Nos. 28 19 655, 29 02 672, 25 32 317 and 28 42 08, in U.S. Pat. No. 4,053,585 and in European Patent Application No. 36 676.

For example, the lipid components, for example phospholipids, for example phosphatidic acid, lecithin or cephalin, and optionally neutral lipids, for example cholesterol, are dissolved together with the lipopeptide in an organic solvent, for example chloroform/methanol. Concentration by evaporation yields a homogeneous film layer. This is dispersed in an aqueous phase, for example by shaking. In this manner multilamellar liposomes are obtained. In the subsequent treatment with ultrasound, depending on the period of exposure to ultrasonic waves unilamellar liposomes can be formed which contain the active ingredient. The liposome suspensions can be used especially for parenteral, for example subcutaneous or intraperitoneal, administration, or also topically, for example intranasally, especially when using the novel lipopeptides as antiviral agents.

The present invention relates especially also to the use of the novel lipopeptides according to formula (I) and the mentioned derivatives thereof in a method for achieving an immunity-stimulating effect, or as prophylactic or therapeutic agents against infectious diseases, or as antiviral agents for humans and animals, the novel compounds preferably being administered in the form of the above-described pharmaceutical preparations.

The present invention thus also includes combinations consisting of one or more compounds according to formula (I) or derivatives thereof, and especially lipopetides of the compound groups (IA) or (IB), and one or more antibiotics. Such combinations are indicated, for example, as already mentioned above, for achieving an increased antiobiotic effect for various infectious conditions. These combinations may contain antibiotics from the group consisting of β-lactams, aminoglycosides, tetracyclines, macrolides, lincomycins, polyene or polypeptide antibiotics, anthracyclines, chloramphenicols, thiamphenicols, cycloserines, rifamycins or fusidic acid. Such combinations may be used preferably in the form of pharmaceutical preparations that contain the two components together with pharmaceutical carriers, such as those specially mentioned above.

The invention thus relates to a method of increasing the antibiotic activity of antibiotics in which an antiobiotic is administered together with a lipopeptide of the formula (I) or one of the mentioned derivatives thereof, it being possible for administration to be carried out separately or simultaneously, for example in the form of the above-mentioned combination preparations. In this method an active or sub-active dose of the antibiotic is used, a single dose being, for example, from approximately 50 to approximately 500 mg depending on the nature of the antibiotic. The lipopeptides according to the present invention are used in this method in single doses of from approximately 5 mg up to approximately half the amount of antibiotic. The lipopeptide can be administered up to 24 hours before or after the antibiotic, but is preferably administered approximately at the same time as the antibiotic.

In this method it is possible to use individual antibiotics or mixtures of antibiotics. As preferred antibiotics there may be mentioned among the β-lactams penicillins, cephalosporins, penems, nocardicins, thienamycins and clavulanic acids. Penicillin antibiotics are especially amoxycillin, ampicillin, carbenicillin, cloxacillin, cyclacillin, dicloxacillin, mecillinam, methicillin, penicillin G, penicillin V, pivampicillin, sulbenicillin, azlocillin, tricarcillin, mezlocillin, pivmecillinam or 6-(4-endo-aza-tricyclo[5.2.2.0$^{2,6}$]undec-8-enyl)-methyleneamino-penicillanic acid. From the group of cephalosporins there may be mentioned, for example, cefaclor, cefazaflur, cefazolin, cefadroxil, cefoxitin, cefuroxime, cephacetril, cephalexin, cephaloglycin, cephaloridines, cephalotin, cefamandole, cephanone, cephapirin, cefatrizine, cephradine, cefroxadin (7β-[D-2-amino-2-(1,4-cyclohexadienyl)-acetamido]-3-methoxy-3-cephem-4-carboxylic acid, cefsulodin, cefotaxime, cefotiam, ceftezol or cefazedone. Of the nocardicins there may be mentioned, for example, nocardicin A and of the thienamycins and clavulanic acids, for example thienamycin and clavulanic acid. Of the amino-glycosides there may be mentioned especially streptomycins, for example streptomycin and streptomycin A, neomycins, for example neomycin B, tobramycins, for example tobramycin or dibekacin, kanamycins (for example mixtures of kanamycin A, B and C) and amikacins, gentamycins (for example mixtures of gentamycin A, $C_1$, $C_2$ or $C_{1a}$), or sisomicins, such as sisomicin or netilmicin, and also lividomycin, ribocamycin and paromomycin. As tetracyclines there may be mentioned especially tetracycline, doxycycline, chlorotetracycline, oxytetracycline and methacycline. As macrolides there may be mentioned, for example, maridomycin, spiramycins, such as spiramycin I, II and III, erythromycins, for example erythromycin, oleandomycins, for example oleandomycin and tetraacetyloleandomycin, and as lincomycins, for example lincomycin and clindamycin.

There may be mentioned as polyene antibiotics especially amphotericin B and the methyl ester thereof or nystatin. As polypeptide antibiotics there may be mentioned especially, for example, colistrin, gramicidin S, polymyxin B, virginamycin, tyrothricin, viomycin and vancomycin. There come into consideration as rifamycins especially rifamycin S, rifamycin SV or rifamycin B or the semi-synthetic derivatives thereof, especially rifampicin.

The following Examples illustrate the abovedescribed invention but are not intended to limit the scope of the invention in any way. Temperatures are given in degrees Centigrade. $R_f$ values are ascertained on thin layer silica gel plates (Merck, Darmstadt, Germany). The composition of the solvent mixtures is, unless specified otherwise, quoted in parts by volume. The concentration, c, of the substance in the solvent (mixture) is, in the case of the optical rotation, indicated as a percentage (weight/volume).

Abbreviations:
Boc: tert.-butoxycarbonyl
Bz: benzyl
DMA: dimethyl acetamide
DMF: dimethylformamide
EEDQ: 2-ethoxy-N-ethoxycarbonyl-1,2-dihydroquinoline
Et: ethyl
Me: methyl
nBu: n-butyl
m.p.: melting point
Su: succinimidyl
tBu: tert.-butyl
Z: benzyloxycarbonyl.

EXAMPLE 1

(a) 4.1 g (3.89 mmol) of palmitoyl-Cys(2[R],3-dilauroyl-oxy-propyl)-Ala-D-Glu(OtBu)-NH$_2$ are dissolved in a mixture of 18 ml of trifluoroacetic acid and 42 ml of methylene chloride. After 6 hours at room temperature, the solution is concentrated by evaporation in vacuo to form a syrup, then triturated with ether, and a colourless, crystalline residue is obtained; this is extracted again with ether and twice recrystallised from ethanol, yielding palmitoyl-Cys(2[R],3-dilauroyloxy-propyl)-Ala-D-Glu-NH$_2$; $R_f$=0.23 (CHCl$_3$:EtOH=9:1), m.p. 158°–161°, $[\alpha]_D^{20}$=−12° (CHCl$_3$:MeOH=1:1; c=1.04).

The starting material is obtained as follows:

(b) 5.4 g (6.67 mmol) of palmitoyl-Cys(2[R],3-dilauroyl-oxy-propyl), 2.2 g (7.1 mmol) of Ala-D-Glu(OtBu)-NH$_2$×HCl and 1.1 g (8.1 mmol) of N-hydroxybenzotriazole are dissolved in a mixture of 120 ml of absolute dimethylformamide and 180 ml of methylene chloride; 1.67 g (8.1 mmol) of dicyclohexyl carbodiimide are added and the pH value of the solution is adjusted to approximately 7 with 1 ml of triethylamine. After 16 hours at room temperature, the whole is concentrated to dryness by evaporation in vacuo. The residue is extracted with water, the extracts are discarded and the residue is twice recrystallised from methanol. Colourless crystals of palmitoyl-Cys(2[R],3-dilauroyloxy-propyl)-Ala-D-Glu(OtBu)-NH$_2$ are obtained; m.p. 196°–198°, $[\alpha]_D^{20} = -11°$ (CHCl$_3$: MeOH=1:1; c=0.98), R$_f$=0.44 (CHCl$_3$:EtOH=9:1).

(c) The palmitoyl-Cys(2[R],3-dilauroyloxy-propyl) used as starting material is obtained from the corresponding benzhydryl ester with trifluoroacetic acid:

8 g of benzhydryl ester are left to stand for 3 hours at room temperature in a mixture of 20 ml of trifluoroacetic acid and 80 ml of methylene chloride, the whole is concentrated by evaporation in vacuo to form a syrup and this is extracted with ice-water. The substance is purified by chromatography over 300 g of silica gel, Merck, using the eluants:
methylene chloride/ethanol=95:5
methylene chloride/ethanol=9:1
chloroform/methanol=7:3

Before the substance is introduced onto the column, the pH value is adjusted to approximately 5 with triethylamine. The fractions of the pure substance, which are at first syrupy after concentration by evaporation and have R$_f$=0.22 (CHCl$_3$:MeOH=9:1), crystallise on the addition of methanol, yielding palmitoyl-Cys(2[R],3-dilauroyloxy-propyl); m.p. 52°–55°, $[\alpha]_D^{20} = -7°$ (dioxan; c=0.65).

EXAMPLE 2

(a) 300 mg of palmitoyl-Cys(2[R],3-dipalmitoyloxy-propyl)-Ala-D-Glu-(Ala-OBz)-NH$_2$ are hydrogenated for 50 hours at 45° in 50 ml of dimethylformamide/tetrahydrofuran (7:3) with 200 mg of palladium/Mohr. The catalyst is filtered off and extraction is carried out with 30 ml of warm solvent mixture. The solutions are concentrated by evaporation in vacuo and the residue is purified over 10 g of silica gel, Merck, using chloroform/methanol (9:1) as eluant. After concentration of the pure fractions by evaporation there are obtained colourless crystals of palmitoyl-Cys-(2[R],3-dipalmitoyloxy-propyl)-Ala-D-Glu(Ala)-NH$_2$ having a decomposition region of 224°–229°, $[\alpha]_D^{20} = -12°$ (CHCl$_3$:MeOH=1:1; c=0.91), R$_f$=0.31 (CHCl$_3$:MeOH=8:2).

The benzyl ester used as starting material is obtained as follows:

(b) 0.6 g (0.659 mmol) of palmitoyl-Cys(2[R],3dipalmitoyloxy-propyl), 257.6 mg (0.659 mmol) of Ala-D-Glu(Ala-OBz)-NH$_2$×HCl, 106.9 mg (0.79 mmol) of N-hydroxybenzotriazole and 92 µl of triethylamine are dissolved in a mixture of 20 ml of absolute dimethylformamide and 50 ml of methylene chloride, and 164 mg (0.79 mmol) of dicyclohexyl carbodiimide are added thereto. After 16 hours at room temperature the reaction solution is concentrated to dryness by evaporation in vacuo and the residue is stirred with 50 ml of methanol at 50°. A first crystalline fraction is obtained and a second fraction crystallises from the mother liquor. Both fractions are recrystallised again from ethyl acetate. There are thus obtained colourless crystals of palmitoyl-Cys(2[R],3-dipalmitoyloxy-propyl)-Ala-D-Glu(Ala-OBz)-NH$_2$; m.p. 180°–184°, R$_f$=0.61 (CHCl$_3$:EtOH=9:1).

(c) The palmitoyl-Cys(2[R],3-dipalmitoyloxy-propyl) used for coupling with the tripeptide is obtained from the corresponding benzhydryl ester analogously to Example 1c in the form of a colourless, crystalline substance having a melting point of 71°–75°, R$_f$=0.45 (CHCl$_3$:MeOH=9:1), $[\alpha]_D^{20} = -4°$ (dioxan; c=0.89).

EXAMPLE 3

3 mg of the lipopeptide palmitoyl-Cys(2[R],3-dilauroyloxy-propyl)-Ala-D-Glu-NH$_2$ (see Example 1) are dissolved together with 27 mg of lecithin in a mixture of chloroform and methanol 2:1. The mixture is then concentrated by evaporation in vacuo in a rotary evaporator, a lipid film being obtained. To this film there is added 0.2 ml of a sterile, pyrogen-free 0.9% NaCl solution "flec-Flac" by VIFOR S.A. of Genf. The solution is exposed to ultrasonic waves for 2 minutes at room temperature, there being produced a suspension of lipid vesicles (liposomes) having a diameter of approximately from 1 to 5 microns, which contain the lipopeptide. This suspension can be administered, for example subcutaneously or intraperitoneally, to mice in doses of 0.1 ml per 10 g body weight.

Similar pharmaceutical preparations for administration to humans can be manufactured in analogous manner.

EXAMPLE 4

500 mg (0.34 mmol) of palmitoyl-Cys(2[R],3-dilauroyl-oxy-propyl)-Ala-D-Gly{Lys(Boc)-Lys(Boc)-Ome}-NH$_2$ are dissolved in a mixture of 5.3 ml of 1.7N hydrochloric acid in absolute ethyl acetate and 12 ml of absolute methylene chloride. After 1 hour at room temperature, the solution is evaporated to dryness and this operation is repeated 3 times using 10 ml of methyl tert.-butyl ether each time. The residue is triturated with acetone and the precipitate is filtered off with suction, and this operation is repeated using warm ethyl acetate to which the same volume of acetone is added before the filtration with suction, yielding palmitoyl-Cys(2[R],3-dilauroyloxy-propyl)-Ala-D-Glu{Lys-Lys-OMe}-NH$_2$×2HCl in the form of colourless crystals with 0.5 mol of water of crystallisation; m.p. 250°–260° (decomposition), $[\alpha]_D^{20} = -18°±1°$ (c=0.849; CHCl$_3$:MeOH=1:1), R$_f$=0.22 (CHCl$_3$:MeOH:H$_2$O:acetic acid=75:25:2:2).

The starting material is obtained as follows:

Stage 4.1

1 g (1.002 mmol) of palmitoyl-Cys(2[R],3-dilauroyloxy-propyl)-Ala-D-Glu-N$_2$, 0.15 g of N-hydroxybenzotriazole, 0.15 g of N-hydroxysuccinimide and 0.5 g of dicyclohexyl carbodiimide are stirred for 3 hours at room temperature in a mixture of 5 ml of dimethylformamide, 20 ml of chloroform and 5 ml of acetonitrile. 0.55 g (1.05 mmol) of Lys(Boc)-Lys(Boc)-OMe×HCl and 0.3 ml of triethylamine are then added. After 40 hours at room temperature, the whole is concentrated by evaporation in vacuo, the residue is stirred with 20 ml of water and filtered with suction. This is repeated with methanol, and the precipitate that remains is recrystallised from MeOH. There are thus obtained colourless crystals of palmitoyl-Cys(2[R],3-dilauroyloxy-propyl)-Ala-D-Glu{Lys(Boc)-Lys(Boc)-Ome}-NH$_2$; m.p. 180°-182°, $[\alpha]_D^{20}=-25°\pm1°$ (c=1.395; CHCl$_3$), R$_f$=0.69 (CHCl$_3$:MeOH=9:1).

EXAMPLE 5

1 g (1.002 mmol) of palmitoyl-Cys(2[R],3-dilauroyloxy-propyl)-Ala-D-Glu-NH$_2$, 0.23 g of N-hydroxysuccinimide, 0.07 g of N-hydroxybenzotriazole and 0.52 g of dicyclohexyl carbodiimide are dissolved in 15 ml of absolute dimethyl acetamide and the whole is allowed to stand for 5 hours at room temperature. A solution of 0.274 g of glycyl taurine and 173 µl of tetramethylguanidine in 10 ml of dimethyl acetamide is then added. After 24 hours at room temperature, a further 100 mg of dicyclohexyl carbodiimide, 100 mg of N-hydroxysuccinimide, 50 mg of glycyl taurine and 90 µl of tetramethylguanidine are added. After a further 24 hours at room temperature, working up is carried out. Concentration by evaporation in vacuo, washing of the residue with 50 ml of hexane and then with 30 ml of acetonitrile, and subsequent digestion three times at 40° with 20 ml of saturated NaCl solution each time yield a residue which is dissolved in CHCl$_3$/MeOH/water (85:15:1) at 40° and chromatographed over silica gel. After elution with CHCl$_3$/MeOH/H$_2$O (70:30:3) and concentration by evaporation in vacuo there is obtained palmitoyl-Cys(2[R],3-dilauroyloxy-propyl)-Ala-D-Glu(Gly-taurine-sodium salt)-NH$_2$×0.82H$_2$O; decomposition point 250°, $[\alpha]_D^{20}=-24°$ (c=1.052; CHCl$_3$:MeOH=1:1), R$_f$=0.256 (CHCl$_3$:MeOH=8:2).

The glycyl taurine used is obtained in known manner by hydrolysis of the sodium salt of N-(Boc-Gly)-taurine with trifluoroacetic acid. The sodium salt of N-(Boc-Gly)-taurine is in turn obtained from Boc-Gly-O-Su and the sodium salt of taurine in 90% aqueous methanol.

EXAMPLE 6

521 mg (0.588 mmol) of octanoyl-Cys(2[R],3-didecanoyloxy-propyl)-Ala-D-Glu(OtBu)-NH$_2$ are stirred for 6 hours at room temperature in 5 ml of methylene chloride containing 20% by volume of trifluoroacetic acid. The solvent is then distilled off in a rotary evaporator at a bath temperature of 40°, the residue is triturated with water, filtered with suction, washed neutral on the suction filter and dried for 4 hours at 40°/0.1 torr. The resulting crude product is recrystallised from ethyl methyl ketone, yielding octanoyl-Cys(2[R,S],3-didecanoyloxy-propyl)-Ala-D-Glu-NH$_2$; m.p.170°-171°, $[\alpha]_D^{20}=-13°$ (c=1.723; CHCl$_3$:methanol=1:1), R$_f$=0.5 (CHCl$_3$:methanol=9:1).

The starting material is obtained as follows:

Stage 6.1

26.8 g (0.16 mol) of caprylic acid chloride in 30 ml of methylene chloride are added dropwise at 20°-25° under a nitrogen atmosphere to 20 g (0.16 mol) of L-cysteine in 150 ml of pyridine and 120 ml of methylene chloride and the whole is then stirred at room temperature for 17 hours. The methylene chloride is removed from the reaction mixture by distillation at approximately 40° in vacuo, and 150 ml of pyridine, 150 ml of DMA and 150 ml of water are added, a homogeneous solution being formed. The reaction mixture is then adjusted to pH=9 with 30% NaOH, stirred for 2 hours at room temperature, adjusted to pH=5 with 2N hydrochloric acid and extracted with ethyl acetate, and the organic phase is dried over sodium sulphate and concentrated by evaporation in a rotary evaporator at 40°-45°, octanoyl-Cys remaining behind in the form of a yellow, viscous oil; R$_f$=0.31 (chloroform:methanol=7:3), $[\alpha]_D^{20}=-16°$ (c=1.06; CHCl$_3$:MeOH=1:1).

Stage 6.2

13.9 g (0.189 mol) of glycerine glycide are added, under nitrogen, to 40.4 g (0.163 mol) of octanoyl-Cys and 52.8 g (0.383 mol) of potassium carbonate in 375 ml of ethanol. Under a weak current of nitrogen, the whole is stirred for 4 hours at 75°-80°, cooled to room temperature, 150 ml of water are added to the suspension and the whole is adjusted to approximately pH=3 with 2N HCl and extracted with ethyl acetate. The organic phase is dried over sodium sulphate and filtered, and the filtrate is concentrated by evaporation, octanoyl-Cys(2[R,S],3-dihydroxy-propyl) remaining behind in the form of a yellow oil; R$_f$=0.23 (CHCl$_3$:MeOH:H$_2$O=65:35:2), $[\alpha]_D^{20}=-6°$ (c=0.995; CHCl$_3$:MeOH=1:1).

Stage 6.3

2.28 g (9.22 mmol) of EEDQ, 1.95 g (6.32 mmol) of Ala-D-Glu(OtBu)-NH$_2$×HCl and 0.77 ml (6.32 mmol) of triethylamine are added to 2.01 g (6.32 mmol) of octanoyl-Cys(2[R,S],3-dihydroxy-propyl) in 40 ml of dimethyl acetamide, whereupon the reaction mixture has pH=7. After stirring for 16 hours at 40°-45°, the solvent is distilled off under a high vacuum at 45°50°. The residue is triturated three times with diethyl ether and three times with ethyl acetate and in each case the liquid phase is decanted off. The insoluble residue is dried for 1 hour at 40° and 1 torr, dissolved in 30 ml of THF/H$_2$O (9:1) at room temperature and, while stirring, precipitated again with 100 ml of H$_2$O. After filtration with suction and drying of this precipitate at 40° and 1 torr there is obtained octanoyl-Cys(2[R,S],3-dihydroxy-propyl)-Ala-D-Glu(OtBu)-NH$_2$; m.p. 184°-186°, R$_f$=0.61 (methylene chloride:methanol=8:2), $[\alpha]_D^{20}=-4°$ (c=0.479; CHCl$_3$:MeOH=1:1).

Stage 6.4

2.5 g (3.6 mmol) of octanoyl-Cys(2[R,S],3-dihydroxypropyl)-Ala-D-Glu(OtBu)-NH$_2$ in a mixture of 18.9 ml (0.23 mol) of pyridine and 18.9 ml of carbon tetrachloride are heated to 55°-60° and at this temperature 37.8 mg (0.31 mmol) of 4-dimethylaminopyridine and 1.7 ml (8.1 mmol) of capric acid chloride are added. The reaction mixture is stirred for 20 hours at 55°-60°, cooled, diluted with 200 ml of methylene chloride, shaken three times with 50 ml of 2N HCl each time, then washed neutral with H$_2$O, and the organic phase is dried over Na$_2$SO$_4$ and concentrated by evaporation. The brown, resinous residue is purified by low pressure chromatography over silica gel (0.040-0.64 mm) using the eluant CH$_2$Cl$_2$:methanol=96:4, yielding octanoyl-Cys(2[R,S],3-didecanoyloxy-propyl)-Ala-D-Glu(OtBu)-NH$_2$; m.p. 144°-146°, $[\alpha]_D^{20}=-10°$ (c=1.017; CHCl$_3$:methanol=1:1), R$_f$=0.64 (CHCl$_3$:methanol=9:1).

EXAMPLE 7

0.972 g (1.03 mmol) of octanoyl-Cys(2[R,S],3-didodecanoyloxy-propyl)-Ala-D-Glu(OtBu)-NH$_2$ are reacted analogously to Example 1a to form octanoyl-Cys(2[R,S],3-didodecanoyloxy-propyl)-Ala-D-Glu- NH$_2$; m.p. 162°, [α]$_D^{20}$ = +12° (c=0.855; chloroform-:methanol=1:1), R$_f$=0.2 (chloroform:methanol=92:8).

The starting material is obtained as follows:

Stage 7.1

1.1 g (1.90 mmol) of octanoyl-Cys(2[R,S],3-dihydroxy-propyl)-Ala-D-Glu(OtBu)-NH$_2$ are reacted analogously to Stage 6.4 with lauric acid chloride to form octanoyl-Cys(2[R,S],3-didodecanoyloxy-propyl)-Ala-D-Glu(OtBu)-NH$_2$; m.p. 140°-141°, [α]$_D^{20}$ = −9° (c=1.352; chloroform:methanol=1:1), R$_f$=0.37 (chloroform:methanol=92:8).

EXAMPLE 8

900 mg (0.902 mmol) of octanoyl-Cys(2[R,S],3-ditetradecanoyloxy-propyl)-Ala-D-Glu(OtBu)-NH$_2$ are reacted analogously to Example 1a to form octanoyl-Cys(2[R,S],3-ditetradecanoyloxy-propyl)-Ala-D-Glu-NH$_2$; m.p. 166°, [α]$_D^{20}$ = −11° (c=1.457; CHCl$_3$:methanol=1:1), R$_f$=0.11 (CHCl$_3$:methanol=92:8).

The starting material can be obtained as follows:

Stage 8.1

1.1 g (1.90 mmol) of octanoyl-Cys(2[R,S],3-dihydroxy-propyl)-Ala-D-Glu(OtBu)-NH$_2$ are reacted with 1.03 g (4.18 mmol) of myristoyl chloride analogously to Stage 6.4 to form octanoyl-Cys(2[R,S],3-ditetradecanoyloxy-propyl)-Ala-D-Glu(OtBu)-NH$_2$; m.p. 140°-141°, [α]$_D^{20}$ = −10° (c=0.648; CHCl$_3$:methanol=1:1), R$_f$=0.5 (CHCl$_3$:methanol=92:8).

EXAMPLE 9

995.3 mg (0.971 mmol) of decanoyl-Cys(2[R,S],3-ditetradecanoyloxy-propyl)-Ala-D-Glu(OtBu)-NH$_2$ are reacted analogously to Example 1a to form decanoyl-Cys(2[R,S],3-ditetradecanoyloxy-propyl)-Ala-D-Glu-NH$_2$; m.p. 154°-155°, [α]$_D^{20}$ = −12° (c=0.922; CHCl$_3$:methanol=1:1), R$_f$=0.41 (CHCl$_3$:methanol=1:1).

The starting material can be obtained as follows:

Stage 9.1

20 g of L-cysteine (0.1652 mol) are reacted with 28.2 g (0.1487 mol) of capric acid chloride analogously to Stage 6.1 to form decanoyl-Cys; m.p. 57°-58°, R$_f$=0.21 (CHCl$_3$:methanol=85:15), [α]$_D^{20}$ = −15° (c=0.814, CHCl$_3$:MeOH=1:1).

Stage 9.2

6.1 g (22.2 mmol) of decanoyl-Cys are reacted analogously to Stage 6.2 to form decanoyl-Cys(2[R,S],3-dihydroxy-propyl); A viscous yellow oil is obtained having R$_f$=0.25 (CHCl$_3$:MeOH=65:35), [α]$_D^{20}$ = −4° (c=0.946; CHCl$_3$:MeOH=1:1).

Stage 9.3

2.62 g (7.49 mmol) of decanoyl-Cys(2[R,S],3-dihydroxy-propyl) are reacted with 2.31 g (1.49 mmol) of Ala-D-Glu(OtBu)-NH$_2$×HCl analogously to Example 1b to form decanoyl-Cys(2[R,S],3-dihydroxy-propyl)-Ala-D-Glu(OtBu)-NH$_2$; m.p. 166°-167°, [α]$_D^{20}$ = −27° (c=0.804; CHCl$_3$:methanol=1:1), R$_f$=0.48 (CH$_2$Cl$_2$:methanol=85:15).

Stage 9.4

907 mg (1.5 mmol) of decanoyl-Cys(2[R,S],3-dihydroxy-propyl)-Ala-D-Glu(OtBu)-NH$_2$ are reacted with 814 mg (3.3 mmol) of myristoyl chloride to form decanoyl-Cys(2[R,S],3-ditetradecanoyloxy-propyl)-Ala-D-Glu(OtBu)NH$_2$; m.p. 138°-139°, [α]$_D^{20}$ = −9° (c=1.234; CHCl$_3$:methanol 1:1), R$_f$=0.51 (CHCl$_3$:methanol=9:1).

EXAMPLE 10

987 mg of decanoyl-Cys(2[R,S],3-didodecanoyloxy-propyl)-Ala-D-Glu(OtBu)-NH$_2$ are reacted analogously to Example 1a to form decanoyl-Cys(2[R,S],3-didodecanoyloxy-propyl)-Ala-D-Glu-NH$_2$; m.p. 180°, [α$_D^{20}$ = −12° (c=1.066; CHCl$_3$:methanol−1:1), R$_f$=0.4 (CHCl$_3$:methanol=92:8).

The starting material can be obtained as follows:

Stage 10.1

604 mg (1 mmol) of decanoyl-Cys(2[R,S],3-dihydroxy-propyl)-Ala-D-Glu(OtBu)-NH$_2$ are reacted with 480 mg (2.2 mmol) of lauric acid chloride analogously to Stage 6.4 to form decanoyl-Cys(2[R,S],3-didodecanoyloxy-propyl)-Ala-D-Glu(OtBu)-NH$_2$; m.p. 146°-147°, [α]$_D^{20}$ = −8° (c=1.246; CHCl$_3$:methanol=1:1), R$_f$=0.62 (CHCl$_3$:methanol=9:1).

EXAMPLE 11

1.5 g (1.75 mmol) of decanoyl-Cys(2[R,S],3-dioctanoyloxy-propyl)-Ala-D-Glu(OtBu)-NH$_2$ are reacted analogously to Example 1a to form decanoyl-Cys(2[R,S],3-dioctanoyloxy-propyl)-Ala-D-Glu-NH$_2$; m.p. 154°-155°, [α]$_D^{20}$ = −15° (c=0.958; CHCl$_3$:methanol=1:1), R$_f$=0.375 (CHCl$_3$:methanol:H$_2$O=80:20:1).

The starting material can be obtained as follows:

Stage 11.1

955.5 mg (1.58 mmol) of decanoyl-Cys(2[R,S],3-dihydroxy-propyl)-Ala-D-Glu(OtBu)-NH$_2$ are reacted analogously to Stage 6.4 with 565 mg (3.475 mmol) of caprylic acid chloride to form decanoyl-Cys(2[R,S],3-dioctanoyloxypropyl)-Ala-D-Glu(OtBu)-NH$_2$; m.p. 165°-167°, [α]$_D^{20}$ = −12°, (c=0.930; CHCl$_3$:methanol=1:1), R$_f$=0.454 (toluene:ethanol=85:15).

EXAMPLE 12

2.912 g (2.841 mmol) of tetradecanoyl-Cys(2[R,S],3-didodecanoyloxy-propyl)-Ala-D-Glu(OtBu)-NH$_2$ are reacted analogously to Example 1a to form tetradecanoyl-Cys(2[R,S],3-didodecanoyloxy-propyl)-Ala-D-Glu-NH$_2$; m.p. 160°-162°, [α]$_D^{20}$ = −12° (c=1.333; CHCl$_3$:methanol=1:1), R$_f$=0.39 (CHCl$_3$:MeOH:H$_2$O=80:20:1).

The starting material is obtained as follows:

Stage 12.1

20 g (0.1652 mol) of Cys are reacted with 36.6 g (0.1487 mol) of myristoyl chloride analogously to Stage 6.1 to form tetradecanoyl-Cys: m.p.=63°-65°, R$_f$=0.13 (CH$_2$Cl$_2$:acetone=8:2).

Stage 12.2

31.0 g (93.5 mmol) of tetradecanoyl-Cys are reacted analogously to Stage 6.2 with 8.3 g (108 mmol) of glycerine glycide to form tetradecanoyl-Cys(2[R,S],3dihydroxy-propyl) (resin); R$_f$=0.19 (CHCl$_3$:methanol=65:35), [α]$_D^{20}$ = +3° (c=1.183; CHCl$_3$:MeOH=1:1).

Stage 12.3

3.0 g (7.39 mmol) of tetradecanoyl-Cys(2[R,S],3-dihydroxy-propyl) are reacted with 2.28 g (7.39 mmol) of Ala-D-Glu(OtBu)-NH$_2$×HCl analogously to Stage 6.3 to form tetradecanoyl-Cys(2[R,S],3-dihydroxy-propyl)-Ala-D-Glu(OtBu)-NH$_2$; m.p. 161°–162°, R$_f$=0.52 (toluene:ethyl acetate:isopropanol:2N acetic acid = 10:35:35:20), $[\alpha]_D^{20} = -19°$ (c=1.112; CHCl$_3$:MeOH=1:1).

Stage 12.4

3.29 g (5.21 mmol) of tetradecanoyl-Cys(2,[R,S],3-dihydroxy-propyl)-Ala-D-Glu(OtBu)-NH$_2$ are reacted with 2.5 g (11.4 mmol) of lauric acid chloride analogously to Stage 6.4 to form tetradecanoyl-Cys(2[R,S],3-didodecanoyloxy-propyl)-Ala-D-Glu(OtBu)-NH$_2$; m.p. 129°–131°, $[\alpha]_D^{20} = -7°$ (c=1.194; CHCl$_3$:methanol=1:1), R$_f$=0.55 (CHCl$_3$:methanol=9:1).

EXAMPLE 13

1.02 g (1.06 mmol) of tetradecanoyl-Cys(2[R,S],3-didecanoyloxy-propyl)-Ala-D-Glu(OtBu)-NH$_2$ are reacted analogously to Example 1a to form tetradecanoyl-Cys(2[R,S],3-didecanoyloxy-propyl)-Ala-D-Glu-NH$_2$; m.p. 166°–167°, $[\alpha]_D^{20} = -13°$, (c=1.13; CHCl$_3$:methanol=1:1), R$_f$=0.3 (CHCl$_3$:methanol:H$_2$O=75:25:1).

The starting material is manufactured as follows:

Stage 13.1

997.7 mg (1.5 mmol) of tetradecanoyl-Cys(2[R,S],3-dihydroxy-propyl)-Ala-D-Glu(OtBu)-NH$_2$ are reacted analogously to Stage 6.4 with 629 mg (3.3 mmol) of capric acid chloride to form tetradecanoyl-Cys(2[R,S],3-didecanoyloxypropyl)-Ala-D-Glu(OtBu)-NH$_2$; m.p. 132°–133°, $[\alpha]_D^{20} = -10°$ (c=0.943; CHCl$_3$:methanol=1:1), R$_f$=0.64 (CHCl$_3$:methanol=9:1).

EXAMPLE 14

1.311 g (1.41 mmol) of tetradecanoyl-Cys(2,[R,S],3-dioctanoyloxy-propyl)-Ala-D-Glu(OtBu)-NH$_2$ are reacted analogously to Example 1a to form tetradecanoyl-Cys(2[R,S],3-dioctanoyloxy-propyl)-Ala-D-Glu-NH$_2$; m.p. 170° $[\alpha]_D^{20} = -13°$ (c=1.201; CHCl$_3$:methanol=1:1), R$_f$=0.43 (CHCl$_3$:methanol:H$_2$O=80:20:0.5).

The starting material is manufactured as follows:

Stage 14.1

998.2 mg (1.58 mmol) of tetradecanoyl-Cys(2[R,S],3-dihydroxy-propyl)-Ala-D-Glu-NH$_2$ are reacted with 565 mg (3.47 mmol) of caprylic acid chloride analogously to Stage 6.4 to form tetradecanoyl-Cys(2[R,S],3-dioctanoyloxy-propyl)-Ala-D-Glu(OtBu)-NH$_2$; m.p. 136°–138°, $[\alpha]_D^{20} = -9°$ (c=0.990; CHCl$_3$:methanol=1:1), R$_f$=0.54 (CHCl$_3$:methanol=9:1).

EXAMPLE 15

565 mg (0.659 mmol) of tetradecanoyl-Cys(2[R,S],3-dihexanoyloxy-propyl)-Ala-D-Glu(OtBu)-NH$_2$ are reacted analogously to Example 1a to form tetradecanoyl-Cys(2[R,S],3-dihexanoyloxy-propyl)-Ala-D-Glu-NH$_2$; m.p. 176°–177°, $[\alpha]_D^{20} = -14°$ (c=1.130; CHCl$_3$:methanol=1:1), R$_f$=0.31 (CHCl$_3$:methanol=8:2).

The starting material is manufactured as follows:

Stage 15.1

1 g (1.58 mmol) of tetradecanoyl-Cys(2[R,S],3-dihydroxy-propyl)-Ala-D-Glu(OtBu)-NH$_2$ are reacted analogously to Stage 6.4 with 466 mg (3.48 mmol) of caproic acid chloride to form tetradecanoyl-Cys(2[R,S],3-dihexanoyloxy-propyl-Ala-D-Glu(OtBu)-NH$_2$; m.p. 144°–145°, $[\alpha]_D^{20} = -12°$ (c=1.281; CHCl$_3$:methanol=1:1), R$_f$=0.43 (CHCl$_3$:methanol=95:5).

EXAMPLE 16

In a manner analogous to that described in Example 1a, palmitoyl-Cys(2[R],3-dilauroyloxy-propyl)-Abu-D-Glu(OtBu)-NH$_2$ is hydrolysed at room temperature for 3 hours with a solution of 3 parts by volume of trifluoroacetic acid in 7 parts by volume of methylene chloride. After analogous working up there is obtained palmitoyl-Cys(2[R],3-dilauroyloxy-propyl)-Abu-D-Glu-NH$_2$ in the form of colourless crystals; m.p. 176°–179°, $[\alpha]_D^{20} = -15°$ (c=0.818; CHCl$_3$:MeOH=1:1), R$_f$=0.155 (CHCl$_3$:MeOH=9:1).

The starting material is manufactured as follows:

Stage 16.1

In a manner analogous to that described in Example 1b, from Abu-D-Glu(OtBu)-NH$_2$×HCl and palmitoyl-Cys(2[R],3-dilauroyloxy-propyl) with EEDQ there is obtained palmitoyl-Cys(2[R],3-dilauroyloxy-propyl)-Abu-D-Glu(OtBu)-NH$_2$ in the form of colourless crystals; m.p. 139°–141°, $[\alpha]_D^{20} = -14°$ (c=0.865; CHCl$_3$:MeOH=1:1), R$_f$=0.7 (CHCl$_3$:MeOH=9:1).

EXAMPLE 17

In a manner analogous to that described in Example 1a, palmitoyl-Cys(2[R],3-dilauroyloxy-propyl)-Val-D-Glu(OtBu)-NH$_2$ is hydrolysed at room temperature for 3 hours with a solution of 3 parts by volume of trifluoroacetic acid and 7 parts by volume of methylene chloride. After analogous working up there is obtained palmitoyl-Cys(2[R],3-dilauroyloxy-propyl)-Val-D-Glu-NH$_2$ in the form of colourless crystals; m.p. 173°–175°, $[\alpha]_D^{20} = -16°$ (c=0.985; CHCl$_3$:MeOH=1:1), R$_f$=0.25 (CHCl$_3$:MeOH=9:1).

The starting material is manufactured as follows:

Stage 17.1

In a manner analogous to that described in Example 1b, from Val-D-Glu(OtBu)-NH$_2$×HCl and palmitoyl-Cys(2[R],3-dilauroyloxy-propyl) with EEDQ there is obtained palmitoyl-Cys(2[R],3-dilauroyloxy-propyl)-Val-D-Glu(OtBu)-NH$_2$ in the form of colourless crystals; m.p. 142°–144°, $[\alpha]_D^{20} = -10°$ (c=0.791; CHCl$_3$:MeOH=1:1), R$_f$=0.77 (CHCL$_3$:MeOH=9:1).

EXAMPLE 18

In a manner analogous to that described in Example 1a, from dodecanoyl-Cys(2[R],3-didecanoyloxy-propyl)-Ala-D-Glu(OtBu)-NH$_2$ with trifluoroacetic acid in methylene chloride there is obtained dodecanoyl-Cys(2[R],3-didecanoyloxypropyl)-Ala-D-Glu-NH$_2$ in the form of colourless crystals; m.p. 152°–154°, $[\alpha]_D^{20} = -16°$ (c=1.185; CHCl$_3$:MeOH=1:1), R$_f$=0.35 (CHCl$_3$:MeOH=85:15).

The starting material is manufactured as follows:

Stage 18.1

In a manner analogous to that described in Stage 6.3, from dodecanoyl-Cys(2[R],3-dihydroxy-propyl) and Ala-D-Glu(OtBu)-NH$_2$×HCl there is obtained dodecanoyl-Cys(2[R],3-dihydroxy-propyl)-Ala-D-Glu(OtBu)-NH$_2$ in the form of colourless crystals; m.p. 177°–179°, $[\alpha]_D^{20} = -27°$ (c=0.864; CHCl$_3$:MeOH=1:1), R$_f$=0.605 (CHCl$_3$:MeOH=5:1).

Stage 18.2

In a manner analogous to that described in Stage 6.4, from dodecanoyl-Cys(2[R],3-dihydroxy-propyl)-Ala-D-Glu(OtBu)-NH$_2$ with decanoyl chloride in pyridine there is obtained dodecanoyl-Cys(2[R],3-didecanoyloxy-propyl)-Ala-D-Glu(OtBu)-NH$_2$ in the form of colourless crystals; m.p. 129°–132°, $[\alpha]_D^{20} = -13°$ (c=0.882; CHCl$_3$:MeOH=1:1), R$_f$=0.59 (CHCl$_3$:MeOH=9:1).

EXAMPLE 19

In a manner analogous to that described in Example 1a, from dodecanoyl-Cys(2[R],3-didodecanoyloxy-propyl)-Ala-D-Glu(OtBu)-NH$_2$ with trifluoroacetic acid in methylene chloride there is obtained dodecanoyl-Cys(2[R],3-didodecanoyloxy-propyl)-Ala-D-Glu-NH$_2$; m.p. 149°–150°, $[\alpha]_D^{20} = -15°$, (c=1.019; CHCl$_3$:methanol=1:1), R$_f$=0.44 (CHCl$_3$:MeOH)=85:15).

The starting material is manufactured as follows:

Stage 19.1

In a manner analogous to that described in Stage 6.4, from dodecanoyl-Cys(2[R],3-dihydroxy-propyl)-Ala-D-Glu(OtBu)-NH$_2$ with dodecanoyl chloride in pyridine there is obtained dodecanoyl-Cys(2[R],3-didodecanoyloxy-propyl)-Ala-D-Glu(OtBu)-NH$_2$ in the form of colourless crystals; m.p. 125°–128°, $[\alpha]_D^{20} = -12°$ (c=0.951; CHCl$_3$:MeOH=1:1), R$_f$=0.425 (CHCl$_3$:MeOH=95:5).

EXAMPLE 20

In a manner analogous to that described in Example 1a, from dodecanoyl-Cys(2[R],3-dioctanoyloxy-propyl)-Ala-D-Glu(OtBu)-NH$_2$ there is obtained dodecanoyl-Cys(2[R],3-dioctanoyloxy-propyl)-Ala-D-Glu-NH$_2$ in the form of colourless crystals; m.p. 156°–158°, $[\alpha]_D^{20} = -17°$ (c=0.969; CHCl$_3$:MeOH=1:1), R$_f$=0.355 (CHCl$_3$:MeOH=85:15).

The starting material is manufactured as follows:

Stage 20.1

In a manner analogous to that described in Stage 6.4, from dodecanoyl-Cys(2[R],3-dihydroxy-propyl)-Ala-D-Glu(OtBu)-NH$_2$ with octanoyl chloride in pyridine there is obtained dodecanoyl-Cys(2[R],3-dioctanoyloxy-propyl)-Ala-Glu(OtBu)-NH$_2$ in the form of colourless crystals; m.p. 130°–132°, $[\alpha]_D^{20} = -13°$ (c=0.874; CHCl$_3$:MeOH=1:1), R$_f$=0.565 (CHCl$_3$:MeOH=95:5).

EXAMPLE 21

From palmitoyl-Cys(2[R],3-dilauroyloxy-propyl) and Ala-D-Glu(Arg-OMe)-NH$_2$×2HCl there is obtained analogously to Example 1b palmitoyl-Cys(2[R],3-dilauroyloxy-propyl)-Ala-D-Glu(Arg-OMe)-NH$_2$×HCl; $[\alpha]_D^{20} = -8°$ (c=0.493; chloroform:methanol=1:1), R$_f$=0.39 (chloroform:methanol:water=70:30:5), R$_f$=0.74 (chloroform:methanol:water:acetic acid=55:47:13:5).

The starting material is obtained as follows:

Stage 21.1

29.79 g (75 mmol) of Boc-Ala-D-Glu-NH$_2$, 9.49 g (82.5 mmol) of N-hydroxysuccinimide and 19.59 g (75 mmol) of Arg-OMe×2HCl are dissolved in 300 ml of absolute dimethylformamide, then, at low temperature, first 8.26 ml (75 mmol) of N-methylmorpholine and then 18.57 g (90 mmol) of dicyclohexyl carbodiimide are added. After stirring for 22 hours at room temperature, the yellow suspension is diluted with 150 ml of ethyl acetate, the insoluble precipitate is filtered off with suction and the filtrate is concentrated to dryness by evaporation. The residue is suspended in 300 ml of distilled water at low temperature, the dicyclohexylurea is filtered off with suction and the filtrate is concentrated to dryness by evaporation. The crude product is purified by counter-current distribution (lower and upper phase each 25 ml) in the system n-butanol:water=1:1, K value (distribution coefficient)=0.40. The material contained in vessels 84–120 after 326 distribution steps is collected, the solvent is concentrated by evaporation in vacuo at 30° and the residue is purified by crystallisation twice from isopropanol and ethyl acetate/diethyl ether (1:1). Boc-Ala-D-Glu(Arg-Ome)-NH$_2$×HCl is obtained in the form of colourless crystals; m.p. 71°, $[\alpha]_D^{20} = -18°$ (c=0.549; methanol), R$_f$=0.28 (ethyl acetate:n-butanol:pyridine:acetic acid:water=42:21:21:6:10), R$_f$=0.64 (chloroform:methanol:water:acetic acid=55.47:13:5).

Stage 21.2

From Boc-Ala-D-Glu(Arg-OMe)-NH$_2$×2HCl there is obtained by cleaving with 5N HCl in ethyl acetate Ala-D-Glu(Arg-OMe)-NH$_2$×2HCl; $[\alpha]_{546}^{20} = -4°$ (c=0.407; methanol), R$_f$=0.16 (chloroform:methanol:water:acetic acid=55:47:13:5), R$_f$=0.03 (ethyl acetate:n-butanol:pyridine:acetic acid:water=42:21:21:6:10).

EXAMPLE 22

From palmitoyl-Cys(2[R],3-dilauroyloxy-propyl)-N(CH$_3$)-CH$_3$)-CO-D-Glu(OtBu)-NH$_2$ and trifluoroacetic acid in methylene chloride there is obtained analogously to Example 1a palmitoyl-Cys(2[R],3-dilauroyloxy-propyl-Me-Ala-D-Glu-NH$_2$; $[\alpha]_D^{20} = -12°$ (c=0.592; chloroform:methanol=1:1), R$_f$=0.67 (chloroform:methanol:water=70:30:5), R$_f$=0.36 (chloroform:isopropanol:acetic acid=70:8:2).

The starting material is obtained as follows:

Stage 22:1

From palmitoyl-Cys(2[R],3-dilauroyloxy-propyl) and Me-Ala-D-Glu(OtBu)-NH$_2$ there is obtained analogously to Example 1b palmitoyl-Cys(2[R],3-dilauroyloxy-propyl)-Me-Ala-D-Glu(OtBu)-NH$_2$; R$_f$=0.31 (chloroform:dimethoxyethane=4:1), R$_f$=0.90 (chloroform:methanol:water=70:30:5).

EXAMPLE 23

From palmitoyl-Cys(2[R],3-dilauroyloxy-propyl) and Ser-D-Glu(OMe)-OMe there is obtained analogously to Example 1b palmitoyl-Cys(2[R],3-dilauroyloxy-propyl)-Ser-D-Glu(OMe)-OMe; $[\alpha]_D^{20} = -12°$ (c=0.470; chloroform), R$_f$=0.91 (chloroform:methanol:water=70:30:5), R$_f$=0.27 (chloroform:dimethoxyethane=4:1).

EXAMPLE 24

From palmitoyl-Cys(2[R,S],3-dilauroyloxy-propyl) and Ala-D-Glu(NH$_2$)-OnBu×HCl there is obtained analogously to Example 1b palmitoyl-Cys(2[R,S],3-dilauroyloxy-propyl)-Ala-D-Glu(NH$_2$)-OnBu; m.p. 156°–159°, $[\alpha]_D^{20} = -8°$ (c=0.631; chloroform), R$_f$=0.82 (n-butanol:acetic acid:water=75:7.5:21), R$_f$=0.12 (chloroform:dimethoxyethane=4:1).

EXAMPLE 25

Palmitoyl-Cys(2[R],3-dilauroyloxy-propyl)-Ala-D-Gla{(OtBu)$_2$}-NH$_2$ is reacted with trifluoroacetic acid in methylene chloride analogously to Example 1a. The resulting residue is dissolved in a small quantity of pyridine and the solution is diluted with double-distilled water in a ratio of 1:10, filtered through a millipore filter (0.45μ) and lyophilised, yielding palmitoyl-Cys(2[R],3-dilauroyloxy-propyl)-Ala-D-Gla-NH$_2$; m.p. 172°–174°, $[\alpha]_D^{20} = -7°$ (c=0.818; pyridine), R$_f$=0.26 (chloroform:methanol:water=70:30:5), R$_f$=0.40 (n-butanol:acetic acid:water=75:7.5:21), R$_f$=0.64 (ethyl acetate:n-butanol:pyridine:acetic acid:water=42:21:21:6:10).

The resulting acid is dissolved in absolute pyridine and, with the exclusion of moisture, is titrated with 2 equivalents of 0.1M methanolic sodium methoxide solution. The whole is diluted in a ratio of 1:10 with double-distilled water, filtered through a millipore filter (0.45μ) and lyophilised, yielding the disodium salt of palmitoyl-Cys(2[R],3-dialauroyloxy-propyl)-Ala-D-Gla-NH$_2$.

The starting material is obtained as follows:

Stage 25.1

From Z-Ala and D,L-Gla{(OtBu)$_2$}-NH$_2$ there is obtained by means of the EEDQ method Z-Ala-D,L-Gla{(OtBu)$_2$}-NH$_2$ in the form of colourless needles; m.p. 119°–120°, $[\alpha]_D^{20} = -13°$ (c=0.891; methanol), R$_f$=0.74 (chloroform:methanol:water=70:30:5), R$_f$=0.68 (n-butanol:pyridine:acetic acid:water=38:24:8:30).

Stage 25.2

10.2 g (20 mmol) of Z-Ala-D,L-Gla{(OtBu)$_2$}-NH$_2$ in 300 ml of methanol are hydrogenated under normal pressure after the addition of 2 g of palladium-on-carbon (10%). The catalyst is filtered off, the filtrate is concentrated by evaporation and the resulting diastereoisomeric mixture is chromatographed as a "free base" over silica gel (60, Merck, 1:100, 15 ml fractions) in the system chloroform:methanol=9:1. Fractions 60–105 contain Ala-L-Gla{(OtBu)$_2$}-NH$_2$ in the form of a colourless oil; $[\alpha]_D^{20} = +1°$ (c=0.944; methanol), R$_f$=0.52 (chloroform:methanol:water=70:30:5). The diastereoisomer contained in fractions 106–200 can be obtained in pure form by careful crystallisation from dimethoxyethane (19 ml). After standing for 3 hours at −10°, the crystalline mass is filtered with suction and washed first with cold dimethoxyethane and then with petroleum ether/diethyl ether (9:1). After drying, Ala-D-Gla{(OtBu)$_2$}-NH$_2$ is obtained in the form of colourless needles; m.p. 139°–140°, $[\alpha]_D^{20} = +13°$ (c=0.931; methanol), R$_f$=0.60 (n-butanol:pyridine:acetic acid:water=38:24:8:30), R$_f$=0.38 (chloroform:methanol:water=70:30:5).

Stage 25.3

1.08 g (2.5 mmol) of palmitoyl-Cys(2[R],3-dihydroxypropyl), 1.13 g (2.75 mmol) of Ala-D-Gla≡(OtBu)$_2$}-NH$_2$ and 0.80 g (3.25 mmol) of EEDQ are dissolved in a mixture of 4.5 ml of dimethylformamide and 1.5 ml of chloroform and the solution is left to stand under nitrogen for 22 hours at room temperature. The reaction solution is concentrated to dryness by evaporation. The residue is chromatographed over 60 times the amount of silica gel [60, Merck, particle size: 0.063–0.200 mm (70–230 mesh ASTM)] in the system chloroform:methanol=95:5 (50 ml fractions). The fractions containing the product are collected. After the readily volatile portions have been evaporated off there remains palmitoyl-Cys(2[R],3-dihydroxy-propyl)-Ala-D-Gla{(OtBu)$_2$}-NH$_2$ in the form of a colourless oil which, on standing at low temperature, crystallises to form druses; $[\alpha]_D^{20} = -30°$ (c=1.004; chloroform), R$_f$=0.42 (chloroform:methanol=9:1), R$_f$=0.88 (chloroform:methanol:water:acetic acid=55:47:13:5).

Stage 25.4

1.42 g (1.80 mmol) of palmitoyl-Cys(2[R],3-dihydroxypropyl)-Ala-D-Gla{(OtBu)$_2$}-NH$_2$ are dissolved in 12 ml of absolute pyridine and, under nitrogen and with the exclusion of moisture, 1.28 ml (5.4 mmol) of lauric acid chloride in 3 ml of chloroform are added. The acid chloride is added dropwise in such a manner that the temperature does not exceed 20°. After standing for 24 hours, 3 ml of methanol are added to the reaction solution and after 30 minutes the whole is concentrated to dryness by evaporation. The resinous residue, consisting of two main components (mono- and di-lauroyl compound), is subjected to flash chromatography (W. Clark Still et al., J. Org. Chem. 43, 2923 [1978]; 17 ml fractions; 0.4 bar) over 200 g of silica gel [60, Merck, particle size 0.040–0.063 mm (230–400 mesh ASTM)] first with chloroform and then with chloroform/methanol mixtures (99:1 to 97:3). From the combined fractions 17 to 190 there is obtained palmitoyl-Cys(2[R],3-dilauroyloxy-propyl)-Ala-D-Gla{(OtBu)$_2$}-NH$_2$ in the form of a colourless oil; $[\alpha]_D^{20} = -16°$ (c=0.762; chloroform), R$_f$=0.42 (chloroform:methanol=9:1), R$_f$=0.93 (chloroform:methanol:water=70:30:5), R$_f$=0.84 (n-butanol:acetic acid:water=75:7.5:21).

From the combined fractions 215–262 there is obtained palmitoyl-Cys(2[R]-hydroxy-3-lauroyloxypropyl)-Ala-Gla{(OtBu)$_2$}-NH$_2$; $[\alpha]_D^{20} = -23°$ (c=0.864, chloroform), R$_f$=0.32 (chloroform:methanol=9:1), R$_f$=0.84 (chloroform:methanol:water=70:30:5).

EXAMPLE 26

From palmitoyl-Cys(2[R]-hydroxy-3-lauroyloxypropyl)-Ala-D-Gla{(OtBu)$_2$}-NH$_2$ there is obtained analogously to Example 1a with trifluoroacetic acid in methylene chloride palmitoyl-Cys(2[R]-hydroxy-3-lauroyloxy-propyl)-Ala-D-Gla-NH$_2$; R$_f$=0.30 (chloroform:methanol:water=70:30:5), R$_f$=0.43 (ethyl acetate:n-butanol:pyridine:acetic acid:water=42:21:21:6:10), $[\alpha]_D^{20} = -22°$ (c=0.318; dimethyl sulphoxide).

EXAMPLE 27

From palmitoyl-Cys(2[R], 3-dilauroyloxy-propyl)-Abu-D-Glu(OtBu)-OtBu there is obtained analogously to Example 1a palmitoyl-Cys(2[R], 3-dilauroyloxy-propyl)-Abu-D-Glu; m.p. 93°–94° (triturated with cyclohexane:ethyl methyl ketone=9:1), $[\alpha]_D^{20} = -7.1°$ (c=0.577; DMF), $[\alpha]_D^{20} = -9.4°$ (c=0.448;

CHCl$_3$:MeOH=1:1), R$_f$=0.54 (CHCl$_3$:MeOH:-H$_2$O=70:30:5), R$_f$=0.86 (CH$_2$Cl$_2$:MeOH:H$_2$O=5:5:1).

The starting material is obtained as follows:

Stage 27.1

From palmitoyl-Cys(2[R], 3-dilauroyloxy-propyl) and Abu-D-Glu(OtBu)-OtBu×HCl there is obtained analogously to Example 1b with the addition of 4-dimethylaminopyridine palmitoyl-Cys(2[R], 3-dialuroyloxy-propyl)-Abu-D-Glu(OtBu)Otbu; m.p. 44°–45° (from CHCl$_3$:MeOH=7:3), $[α]_D^{20}$= −2.9° (c=0.381; DMF), $[α]_D^{20}$= −7.1° (c=0.325; CHCl$_3$:MeOH=1:1), R$_f$=0.46 (CH$_2$Cl$_2$:MeOH=95:5), R$_f$=0.10 (CHCl$_3$), R$_f$=0.91 (ethyl acetate).

EXAMPLE 28

From palmitoyl-Cys(2[R], 3-dilauroyloxy-propyl)-D-Ala-Ala-D-Glu(OtBu)-NH$_2$ there is obtained analogously to Example 1a palmitoyl-Cys(2[R], 3-dilauroyloxy-propyl)-D-Ala-Ala-D-Glu-NH$_2$, m.p. 173°–174° (from acetonitrile), $[α]_D^{20}$= −6.4 (c=1.018; DMF), $[α]_D^{20}$= −6.8° (c=0989; CHCl$_3$:MeOH=1:1), R$_f$=0.67 (CHCl$_3$:MeOH:H$_2$O=70:30:5), R$_f$=0.40 (CHCl$_3$:MeOH=4:1).

The starting material is obtained as follows:

Stage 28.1

From palmitoyl-Cys(2[R], 3-dihydroxy-propyl) and D-Ala-Ala-D-Glu(OtBu)-NH$_2$×HCl there is obtained and analogously to Stage 6.3 palmitoyl-Cys(2[R], 3-dihydroxy-propyl)-D-Ala-Ala-D-Glu(OtBu)-NH$_2$; m.p. 209°–210° (from ethyl acetate), $[α]_D^{20}$= +0.2° (c=0.655; DMF), $[α]_D^{20}$= −7.8° (c=0.934; CHCl$_3$:MeOH=1:1), R$_f$=0.77 (CHCl$_3$:MeOH:-H$_2$O=70:30:5), R$_f$=0.82 (CHCl$_3$:MeOH=7:3).

Stage 28.2

From palmitoyl-Cys(2[R], 3-dihydroxy-propyl)-D-Ala-Ala-D-Glu(OtBu)-NH$_2$ there is obtained analogously to Stage 6.4 palmitoyl-Cys(2[R], 3-dilauroyloxy-propyl)-D-Ala-Ala-D-Glu(OtBu)-NH$_2$; m.p. 147°–148° (from acetone), $[α]_D^{20}$= −5.3° (c=1.079; DMF), $[α]_D^{20}$= −7.8° (c=1.128; CHCl$_3$:MeOH=1:1), R$_f$=0.42 (CHCl$_3$:MeOH=9:1), R$_f$=0.51 (ethyl acetate).

EXAMPLE 29

From palmitoyl-Cys(2[R,S],3-dilauroyloxy-propyl) and Abu-D-Glu(OMe)-OMe×HCl there is obtained analogously to Example 1b with the addition of N-methylmorpholine palmitoyl-Cys(2[R,S], 3-dilauroyloxy-propyl)-Abu-D-Glu(OMe)-OMe; m.p. 89°–91° (from acetonitrile), $[α]_D^{20}$= −1.8° (c=0.569; DMF), $[α]_D^{20}$= −9.5° (c=0.474; CHCl$_3$:MeOH=1:1), R$_f$=0.34 (CHCl$_3$:ethyl acetate=7.3), R$_f$=0.95 (CHCl$_3$:MeOH=9:1).

EXAMPLE 30

While stirring and cooling with ice, an ethereal diazomethane solution is added to 1.01 g (0.001 mol) of palmitoyl-Cys(2[R], 3-dilauroyloxy-propyl)-Abu-D-Glu in 30 ml of methanol until the yellow colour remains constant. The mixture is left in the ice bath for a further 30 minutes and the excess diazomethane is then destroyed by the addition of a few drops of glacial acetic acid. After concentration by evaporation in vacuo the resulting crude dimethyl ester is twice recrystallised from acetonitrile. Palmitoyl-Cys(2[R], 3-dilauroyloxy-propyl)-Abu-D-Glu(OMe)-OMe is obtained in the form of colourless crystals; R$_f$=0.34 (CHCl$_3$:ethyl acetate=7:3), R$_f$=0.95 (CHCl$_3$:MeOH=9:1).

EXAMPLE 31

From palmitoyl-Cys(2[R,S], 3-dilauroyloxy-propyl)-Ala-D-Glu[Lys(Boc)-D-Ala-OtBu]-OtBu and trifluoroacetic acid in methylene chloride there is obtained analogously to Example 1a palmitoyl-Cys(2[R,S], 3-dilauroyloxy-propyl)-Ala-D-Glu(Lys-D-Ala)-OH; $[α]_D^{20}$= −14° (c=0.163; dichloromethane:ethanol=1:1), R$_f$=0.15 (chloroform:methanol:water=70:30:5), R$_f$=0.16 (ethyl acetate:n-butanol:pyridine:acetic acid:water=42:21:21:6:10), R$_f$=0.58 (chloroform:methanol:water:acetic acid=55:47:13:5).

The starting material is obtained as follows:

Stage 31.1

From palmitoyl-Cys(2[R,S], 3-dialauroyloxy-propyl) and Ala-D-Glu[Lys(Boc)-D-Ala-OtBu]-OtBu there is obtained analogously to Example 1b palmitoyl-Cys(2[R,S],3-dialauroyloxy-propyl)-Ala-D-Glu[Lys(-Boc)-D-Ala-OtBu]-OtBu; $[α]_D^{20}$= −14° (c=1.9; dichloromethane), R$_f$=0.94 (chloroform:methanol:-water=70:30:5), R$_f$=0.28 (chloroform:dimethoxyethane=4:1).

EXAMPLE 32

615 mg (1 mmol) of palmitoyl-Cys-Ala-D-Glu(OtBu)-NH$_2$, 645 mg (1.1 mmol) of 1-tosyl-2,3-didodecanoyl-D-glycerine and 1.4 g of dry potassium carbonate are heated in 30 ml of absolute acetonitrile under nitrogen for 15 hours at 75°. After the mixture has been concentrated by evaporation, taken up in methylene chloride and extracted by shaking several times with water there is obtained a reaction mixture in the organic phase which, after drying with Na$_2$SO$_4$, filtration and concentration by evaporation, is purified by chromatography over silica gel with CHCl$_3$/EtOH (9:1) yielding the palmitoyl-Cys(2[R], 3-dilauroyloxy-propyl)-Ala-D-Glu(OtBu)-NH$_2$ described in Example 1b. The starting material, palmitoyl-Cys-Ala-D-Glu(OtBu)-NH$_2$, is obtained in known manner from palmitoyl-Cys(trityl)-Ala-D-Glu(OtBu)-NH$_2$ by treatment with mercury(II) chloride in acetic acid [J. Am. Chem. Soc. 87, 4922 (1965); J. Org. Chem. 35, 4148 (1970)] and subsequent cleaving of the mercury mercaptide with H$_2$S. The compound is used in the crude state for the further reaction with the glycerine tosylate.

1-tosyl-2,3-didodecanoyl-D-glycerine is obtained in known manner from 1,2-isopropylidene-glycerine and tosyl chloride in pyridine, followed by hydrolysis with 80% acetic acid to form 1-tosyl-D-glycerine which is acylated in known manner with dodecanoic acid chloride. The compound is a syrup which crystallises in an ice bath but quickly melts again above 0° C.

EXAMPLE 33

From palmitoyl-Cys(2[R], 3-dilauroyloxy-propyl)-Ala-D-Glu-NH$_2$ and alanyl-taurine there is obtained analogously to Example 5 palmitoyl-Cys(2[R], 3-dialauroyloxy-propyl)-Ala-D-Glu(Ala-taurine)-NH$_2$ as a hydrate which is partially in the form of its sodium salt (0.12 mole Na$^+$); decomposition above 250°, $[α]_D^{20}$= −20.2°±1.1° (c=0.887; CHCl$_3$:MeOH=1:1), R$_f$=0.3 (CHCl$_3$:MeOH=8:2).

Alanyl-taurine used as a starting material is obtained in known manner from Boc-Ala-taurine-sodium salt and trifluoroacetic acid in the form of an internal salt; m.p.>260°, $[\alpha]_D^{20} = +8.2 \pm 1°$ (c=1.049, water), $R_f = 0.26$ (n-butanol:pyrine:Conc. ammonia:water=40:24:0.6:30).

EXAMPLE 34

Alveolar rat macrophages are obtained by lung lavage, plated out and incubated in vitro from 24 hours either with liposomes that are charged with the active ingredient, or with the active ingredient in physiological salt solution (phosphate buffered saline, PBS), $^{125}$I-marked tumour cells are added and incubation is continued for a further 72 hours. Subsequently the dead tumour cells are washed away and the number of tumour cells still living is determined on the basis of their radioactivity. The macrophage activation is assessed on the basis of the cytotoxicity, that is to say according to the proportion of tumour cells dead at the end of the test. The specific cytotoxicity [%] is calculated as follows:

$$100 \left[ 1 - \frac{\text{cpm in tumor cells incubated with macrophages and active ingredient}}{\text{cpm in tumor cells incubated with macrophages and PBS}} \right]$$

Further details of the above-mentioned test method are described in I. J. Fidler et al., J. Biol. Response Modifiers 1, 43-55 (1982).

The results are given in the following table:

\* = R
\*\* = R or S
\*\*\* = R in which
each of $R_a^1$ and $R_b^1$, independently of the other, represents an aliphatic or cycloaliphatic-aliphatic hydrocarbon radical having from 7 to 21 carbon atoms that is unsubstituted or substituted by hydroxy or epoxy, or
one of the radicals $R_a^1$-CO- and $R_b^1$-CO- represents hydrogen and the other of the radicals $R_a^1$-CO- and $R_b^1$-CO- represents an acyl radical, wherein $R_a^1$ and $R_b^1$ have the meanings given above,
$R^2$ represents an aliphatic or cycloaliphtic-aliphatic hydrocarbon radical having from 1 to 21 carbon atoms that is unsubstituted or substituted by hydroxy or epoxy,
n=0 or 1,
$As°$ represents a radical of the formula -O-Kw-CO- or -NH-Kw-CO- wherein Kw represents an aliphatic hydrocarbon radical having a maximum of 12 carbon atoms,
$As^1$ represents an α-amino acid selected from glycine, alanine, α-methyl-alanine, N-methyl-alanine, serine, α-aminobutyric acid, valine or leucine,
each of $Z^1$ and $Z^2$, independently of the other, represents hydroxy or the N-terminal radical of an α-

| active ingredient | described in the application | | | Specific cytotoxicity [%] | | | | | | | |
|---|---|---|---|---|---|---|---|---|---|---|---|
| | | | | Active ingredient in 0.2 ml of PBS μg/culture | | | | Active ingredient in 100 μg of lipsomes per 0.2 ml μg/culture | | | |
| | Example | page | line | 0 | 0.02 | 0.2 | 2 | 0 | 0.02 | 0.2 | 2 |
| A | 1 | 57 | 9-10 | 0 | not tested | 20 | 65 | 18 | not tested | 57 | 69 |
| C | 8 | 64 | 30-31 | 0 | 38 | 47 | 64 | 19 | 27 | 38 | 66 |
| D | 13 | 68 | 13-14 | 0 | 8 | 31 | 69 | 8 | 10 | 26 | 65 |
| E | 9 | 65 | 13-14 | 0 | 50 | 42 | 39 | 8 | 52 | 53 | 60 |
| F | 12 | 67 | 12-13 | 0 | 22 | 46 | 79 | 19 | 21 | 15 | 31 |
| G | 5 | 61 | 22-24 | 0 | 62 | 66 | 69 | 34 | 39 | 53 | 80 |
| H | 7 | 64 | 15-16 | 0 | 36 | 36 | 70 | 3 | 55 | 49 | 55 |
| I | 20 | 72 | 7-8 | 0 | 25 | 29 | 34 | 3 | 25 | 43 | 48 |
| J | 19 | 71 | 25-26 | 0 | 29 | 39 | 21 | 6 | 22 | 29 | 18 |
| K | 21 | 72 | 23-24 | 0 | 39 | 68 | 74 | 10 | 17 | 32 | 37 |
| L | 25 | 75 | 4-5 | 0 | 55 | 67 | 88 | 10 | 12 | 9 | 25 |
| M | 16 | 69 | last line | 0 | 42 | 38 | 82 | 10 | 32 | 68 | 62 |
| N | 17 | 70 | 18-19 | 0 | 36 | 51 | 79 | 10 | 18 | 78 | 16 |
| O | 22 | 74 | 1-2 | 0 | 64 | 42 | 89 | 21 | 21 | 21 | 58 |
| P | 31 | 80 | 5-6 | 0 | 76 | 79 | 65 | 7 | 21 | 15 | 59 |
| Q | 27 | 78 | 4 | 0 | 62 | 38 | 56 | 15 | 51 | 91 | 87 |
| R | 28 | 78 | 22-23 | 0 | 0 | 84 | 51 | 15 | 20 | 18 | 86 |

We claim:

1. Lipopeptides of the formula

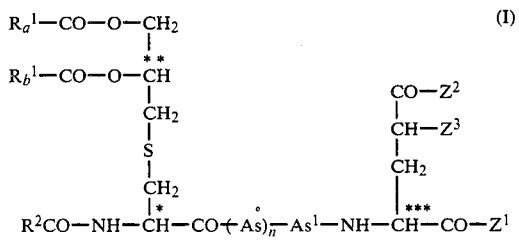

aminocarboxylic acid selected from lysine, ornithine, α,α'-diamino-pimelic acid, glycine, D- and L-alanine, D-asparagine, lanthionine or arginine, of an ω-amino-$C_{2-3}$-alkanesulphonic acid or of a peptide having a maximum of 6 amino acids selected from lysine, ornithine, α,α'-diamino-pimelic acid, glycine, D- and L-alanine, D-asparagine, lanthionine, arginine and ω-amino-$C_{2-3}$-alkanesulphonic acids, and represents hydrogen or -CO-$Z^4$, wherein $Z^4$ represents hydroxy or the N-terminal radical of an α-amino acid selected from lysine, ornithine, α,α'-diamino-pimelic acid, glycine, D- and L-alanine, D-asparagine, lanthionine or arginine, of a ω-amino-$C_{2-3}$-alkanesulphonic acid or of a peptide having a maximum of 6 amino acids selected from lysine, ornithine, α,α'-diamino-pimelic acid, glycine, D- and L-alanine, D-asparagine, lanthionine, arginine and ω-amino-$C_{2-3}$-alkanesulphonic acids, and the amides and esters of such compounds that contain carboxy groups, wherein the centers of asymmetry designated by *,  and * have the absolute configurations indicated, and the configuration at an asymmetric carbon atom carrying the group $Z^3$ may be R or S, and corresponding diastereoisomeric mixtures, as well as salts of such compounds having at least one salt-forming group and optionally complex salts of these compounds.

2. Lipopeptides of the formula I according to claim 1, wherein each of $R_a^1$, $R_b^1$ and $R^2$, independently of the other, represents an aliphatic hydrocarbon radical having from 7 to 21 carbon atoms or one of the radicals $R_a^1$-CO- and $R_b^1$-CO- represents hydrogen and the other of the radicals $R_a^1$-CO- and $R_b^1$-CO- represents an acyl radical, wherein $R_a^1$ and $R_b^1$ have the meanings given above, and $R^2$ has the meaning given above, n=O, $As^1$ represents an α-amino acid selected from the group consisting of Gly, Ala, Ser, Abu, Val, αMeAla and Leu, $Z^1$ represents hydroxy, the N-terminal radical of an amino acid selected from the group consisting of Lys, Orn, Dpm, Gly, Ala, D-Asn and D-Ala, an ω-amino-$C_{2-3}$-alkanesulphonic acid or a peptide consisting of 2 acids selected from the group consisting of Lys, Orn, Dpm, Gly, Ala, D-Asn, D-Ala and an ω-amino-$C_{2-3}$-alkanesulphonic acid, $Z^2$ represents hydroxy, the N-terminal radical of an amino acid selected from the group consisting of Lys, Orn, Dpm, Lan, Gly or Ala, an ω-amino-$C_{2-3}$-alkanesulphonic acid or a peptide consisting of 2 acids selected from the group consisting of Lys, Orn, Dpm, Lan, Gly, Ala or an ω-amino-$C_{2-3}$-alkanesulphonic acid, $Z^3$ represents hydrogen or -CO-$Z^4$, wherein $Z^4$ represents hydroxy or the N-terminal radical of an amino acid selected from the group consisting of Lys, Orn, Dpm, Lan, Gly or Ala, an ω-amino-$C_{2-3}$-alkanesulphonic acid or a peptide consisting of 2 acids selected from the group consisting of Lys, Orn, Dpm, Lan, Gly, Ala and an ω-amino-$C_{2-3}$-alkanesulphonic acid, and the esters of aliphatic alcohols having from 1 to 7 carbon atoms or the esters of $C_{1-7}$-alkanoyloxymethyl alcohols, $C_{1-7}$-alkanoyloxyethyl alcohols, ($C_{3-8}$-cycloalkyl)-carbonyloxymethyl, alcohols, ($C_{3-8}$-cycloalkyl)-carbonyloxyethyl alcohols, propyleneglycol, glycerin, or of a $C_{1-7}$-alkoxy-, $C_{1-7}$-alkylamino-, di-($C_{1-7}$-alkyl)-amino or halo-phenol and unsubstituted amides or amides of $C_{1-7}$-alkylamines, pyrrolidine, piperidine or piperazine of such compounds that contain carboxy groups, as well as pharmaceutically acceptable salts of such compounds having at least one salt-forming group.

3. Lipopeptides of the formula I according to claim 1, in which the radicals $R_a^1$-CO-, $R_b^1$-CO- and $R^2$-CO-, independently of each other, are derived from caprylic, pelargonic, capric, undecylic, lauric, myristic, palmitic, margaric, stearic, arachidic, behenic, oleic, elaidic, linoleic, α- or β-eleostearic, stearolic or α-linolenic acid, n represents zero, $As^1$ represents an α-amino acid selected from glycine, alanine, α-methyl-alanine, N-methyl-alanine, serine, α-aminobutyric acid, valine or leucine, $Z^1$ represents amino, hydroxy or lower alkoxy, $Z^2$ represents the N-terminal radical of a dipeptide the N-terminal acid of which is selected from lysine, orthinine, α,α'-diamino-pimelic acid, glycine, D- and L-alanine, D-asparagine, lanthionine and arginine, and the remaining acid of which is selected from an ω-amino-$C_{2-3}$-alkanesulphonic acid, and $Z^3$ represents hydrogen, as well as pharmaceutically acceptable salts thereof.

4. Lipopeptides of the formula I according to claim 1, wherein each of the radicals $R_a^1$-CO-, $R_b^1$-CO- and $R^2$-CO-, independently of the other, represents the acyl radical of caprylic acid, capric acid, lauric acid, myristic acid, palmitic acid, stearic acid or oleic acid, n represents O, $As^1$ represents an α-amino acid selected from L-alanine, L-N-methyl-alanine, L-α-aminobutyric acid, L-valine or L-serine, $Z^1$ represents amino, hydroxy or lower alkoxy, $Z^2$ represents hydroxy, lower alkoxy, amino, the N-terminal radical of L-alanine, the N-terminal radical of L-alanine-benzylester, the N-terminal radical of L-lysyl-L-lysine or or a lower alkyl ester thereof, the N-terminal radical of glycyl-taurine or of a pharmaceutically acceptable salt thereof, the N-terminal radical of L-arginine or of a lower alkyl ester thereof, or the N-terminal radical of L-lysyl-D-alanine, and $Z^3$ represents hydrogen, as well as pharmaceutically acceptable salts thereof.

5. Lipopeptides of the formula I according to claim 1, wherein each of the radicals $R_a^1$-CO-, $R_b^1$-CO- and $R^2$-CO-, independently of the other, represents the acyl radical of caprylic acid, capric acid, lauric acid, myristic acid, palmitic acid, stearic acid or oleic acid, n represents O, $As^1$ represents an α-amino acid selected from L-alanine, L-N-methyl-alanine, L-α-aminobutyric acid, or L-valine, $Z^1$ represents amino or hydroxy, $Z^2$ represents hydroxy, the N-terminal radical of L-alanine, the N-terminal radical of the methylester of L-lysyl-L-lysine, the N-terminal radical of glycyl-taurine or of a pharmaceutically acceptable salt thereof, the N-terminal radical of the methylester of L-arginine or the N-terminal radical of L-lysyl-D-alanine, and $Z^3$ represents hydrogen, as well as pharmaceutically acceptable salts thereof.

6. Lipopeptides of the formula I according to claim 1, wherein each of the radicals $R_a^1$-CO-, $R_b^1$-CO- and $R^2$-CO-, independently of the other, represents the acyl radical of caprylic acid, capric acid, lauric acid, myristic acid, palmitic acid, stearic acid or oleic acid, n represents O, $As^1$ represents an α-amino acid selected from L-alanine, L-N-methyl-alanine, L-α-aminobutyric acid, or L-valine, $Z^1$ represents amino or hydroxy, $Z^2$ represents the N-terminal radical of a dipeptide, the N-terminal acid of which is selected from glycine and L-alanine and the remaining acid of which is a ω-amino-$C_{2-3}$-alkanesulphonic acid, and $Z^3$ represents hydrogen, as well as pharmaceutically acceptable salts thereof.

7. Palmitoyl-Cys(2[R],3-dilauroyloxy-propyl)-Ala-D-Glu-(Gly-taurine)-NH$_2$ or a pharmaceutically acceptable salt thereof according to claim 1.

8. Palmitoyl-Cys(2[R],3-dilauroyloxy-propyl)-Ala-D-Glu-NH$_2$ or a pharmaceutically acceptable salt thereof according to claim 1.

9. Palmitoyl-Cys(2[R],3-dilauroyloxy-propyl)-Ala-D-Glu(Ala-taurine)-NH$_2$ or a pharmaceutically acceptable salt thereof according to claim 1.

10. Compounds according to claim 1 in which an amino acid $As^1$ is selected from the group consisting of Gly, Ala, Ser, Abu, Val, αMeAla and Leu, an amino acid in the radical $Z^1$ is selected from the group consisting of Lys, Orn, Dpm, Gly, Ala, D-Asn and D-Ala, and an amino acid in the radical(s) $Z^2$ and/or $Z^4$ is selected from the group consisting of Lys, Orn, Dpm, Lan, Gly or Ala, a peptide radical $Z^1$, $Z^2$ or $Z^4$ consisting of 2 amino acids selected in such a manner, and salts of such compounds having at least one salt-forming group.

11. Compounds according to claim 1 in which each of $Z^1$ and $Z^2$ in formula (I), independently of the other, represents hydroxy or the radical of an amino acid selected from lysine, ornithine, $\alpha,\alpha'$-diamino-pimelic acid, glycine, D- and L-alanine, D-asparagine, lanthionine, arginine or an $\omega$-amino-$C_{2-3}$-alkanesulphonic acid, and $Z^3$ represents hydrogen or -CO-$Z^4$ wherein $Z^4$ represents hydroxy or the radical of an amino acid selected from lysine, ornithine, $\alpha,\alpha'$-diamino-pimelic acid, glycine, D- and L-alanine, D-asparagine, lanthionine, arginine or an $\omega$-amino-$C_{2-3}$-alkanesulphonic acid, and salts of such compounds having at least one salt-forming group.

12. Compounds according to claim 10 which each of $Z^1$ and $Z^2$ in formula (I), independently of the other, represents hydroxy or the radical of an amino acid in accordance with claim 4, and $Z^3$ represents hydrogen or -CO-$Z^4$ wherein $Z^4$ represents hydroxy or the radical of an in amino acid in accordance with claim 4, and salts of such compounds having at least one salt-forming group.

13. Compounds according to claim 11 in which $Z^1$ in formula (I) represents an amino acid radical that is selected from the group consisting of -Lys, -Orn, -Dpm, -Gly, -Ala, -D-Ala and -D-Asn, and $Z^2$ and/or $Z^4$ represent an amino acid radical that is selected from the group consisting of -Lys, -Orn, -Dpm, -Lan, -Gly and -Ala, and salts of such compounds having at least one salt-forming group.

14. Compounds according to claim 12 in which $Z^1$ in formula (I) represents an amino acid radical that is selected from the group consisting of -Lys, -Orn, -Dpm, -Gly, -Ala, -D-Ala and -D-Asn, and $Z^2$ and/or $Z^4$ represent an amino acid radical that is selected from the group consisting of -Lys, -Orn, -Dpm, -Lan, -Gly and -Ala, and salts of such compounds having at least one salt-forming group.

15. Compounds according to claim 1 in which the acyl radicals $R_a{}^1$-CO-, $R_b{}^1$-CO- and $R^2$-CO- are derived from saturated or unsaturated fatty acids having from 8 to 16 carbon atoms or (in the case of $R^2$-CO-) from 2 to 16 carbon atoms, and salts of such compounds having at least one salt-forming group.

16. Compounds according to claim 10 in which the acyl radicals $R_a{}^1$-CO-, $R_b{}^1$-CO- and $R^2$-CO- are derived from saturated or unsaturated fatty acids having from 8 to 16 carbon atoms or (in the case of $R^2$-CO-) from 2 to 16 carbon atoms, and salts of such compounds having at least one salt-forming group.

17. Compounds according to claim 12 in which the acyl radicals $R_a{}^1$-CO-, $R_b{}^1$-CO- and $R^2$-CO- are derived from saturated or unsaturated fatty acids having from 8 to 16 carbon atoms or (in the case of $R^2$-CO-) from 2 to 16 carbon atoms, and salts of such compounds having at least one salt-forming group.

18. Compounds according to claim 1 in which the acyl radicals $R_a{}^1$-CO-, $R_b{}^1$-CO- and $R^2$-CO- are derived from caprylic, pelargonic, capric, undecylic, lauric, myristic, palmitic, margaric, stearic, arachidic, behenic, oleic, elaidic, linoleic, $\alpha$- or $\beta$-eleostearic, stearolic or $\alpha$-linolenic acid or, in the case of $R^2$-CO-, also from acetic, propionic, butyric, oenanthic or caproic acid, and salts of such compounds having at least one salt-forming group.

19. Compounds according to claim 10 in which the acyl radicals $R_a{}^1$-CO-, $R_b{}^1$-CO- and $R^2$-CO- are derived from caprylic, pelargonic, capric, undecylic, lauric, myristic, palmitic, margaric, stearic, arachidic, behenic, oleic, elaidic, linoleic, $\alpha$- or $\beta$-eleostearic, stearolic or $\alpha$-linolenic acid or, in the case of $R^2$-CO-, also from acetic, propionic, butyric, oenanthic or caproic acid, and salts of such compounds having at least one salt-forming group.

20. Compounds according to claim 12 in which the acyl radicals $R_a{}^1$-CO-, $R_b{}^1$-CO- and $R^2$-CO- are derived from caprylic, pelargonic, capric, undecylic, lauric, myristic, palmitic, margaric, stearic, arachidic, behenic, oleic, elaidic, linoleic, $\alpha$- or $\beta$-eleostearic, stearolic or $\alpha$-linolenic acid or, in the case of $R^2$-CO-, also from acetic, propionic, butyric, oenanthic or caproic acid, and salts of such compounds having at least one salt-forming group.

21. Compounds according to claim 1 in which the acyl radicals $R_a{}^1$-CO-, $R_b{}^1$-CO- and $R^2$-CO- are derived from saturated or unsaturated cycloaliphatic-aliphatic carboxylic acids having from 8 to 16 carbon atoms or, in the case of $R^2$-CO-, from 2 to 16 carbon atoms in the aliphatic moiety and, at any position in the carbon chain, are substituted by a cycloalkyl or cycloalkenyl ring having from 3 to 8 carbon atoms or interrupted by a cycloalkylene or cycloalkylene radical having from 3 to 8 carbon atoms, and salts of such compounds having at least one salt-forming group.

22. Compounds according to claim 21 in which the acyl radicals are derived from dihydrosterculic, malvalic, hydnocarpic or chaulmoogric acid, and salts of such compounds having at least one salt-forming group.

23. Compounds according to claim 1 in which $R_a{}^1$-CO- and $R_b{}^1$-CO- are different from $R^2$-CO- and $R_a{}^1$-CO- and $R_b{}^1$-CO- represent lauroyl, myristoyl, palmitoyl or stearoyl and $R^2$-CO- represents stearoyl, myristoyl, lauroyl, caprinoyl or capryloyl, and salts of such compounds having at least one salt-forming group.

24. Compounds according to claim 2 in which $R_a{}^1$-CO- and $R_b{}^1$-CO- are different from $R^2$-CO- and $R_a{}^1$-CO- and $R_b{}^1$-CO- represent lauroyl, myristoyl, palmitoyl or stearoyl and $R^2$-CO- represents stearoyl, myristoyl, lauroyl, caprinoyl or capryloyl, and salts of such compounds having at least one salt-forming group.

25. Compounds according to claim 12 in which $R_a{}^1$-CO- and $R_b{}^1$-CO- are different from $R^2$-CO- and $R_a{}^1$-CO- and $R_b{}^1$-CO- represent lauroyl, myristoyl, palmitoyl or stearoyl and $R^2$-CO- represents stearoyl, myristoyl, lauroyl, caprinoyl or capryloyl, and salts of such compounds having at least one salt-forming group.

26. Esters according to claim 1 in which the ester groups are derived from optionally substituted, aliphatic, araliphatic, aromatic or heterocyclic alcohols, and salts of such compounds having at least one salt-forming group.

27. Esters according to claim 1 in which aliphatic ester groups are derived from lower aliphatic alcohols having from 1 to 7 carbon atoms, araliphatic ester components are derived from monocyclic-lower aliphatic alcohols having from 1 to 7 carbon atoms in the aliphatic moiety, aromatic ester components are derived from $C_{1-7}$-alkoxy-, $C_{1-7}$-alkylamino- or di-($C_{1-7}$)-alkylmaino- or halo-phenols and heterocyclic ester groups are derived from tetrahydrofuranol or tetrahydropyranol, and salts of such compounds having at least one salt-forming group.

28. Esters according to claim 18 in which aliphatic ester groups are derived from lower aliphatic alcohols having from 1 to 7 carbon atoms, araliphatic ester components are derived from monocyclic-lower aliphatic alcohols having from 1 to 7 carbon atoms in the aliphatic moiety, aromatic ester components are derived from $C_{1-7}$-alkoxy-, $C_{1-7}$-alkylamino- or di-($C_{1-7}$)-alkylamino- or halo-phenols and heterocyclic ester groups are derived from tetrahydrofuranol or tetrahydropyranol, and salts of such compounds having at least one salt-forming group.

29. Esters according to claim 25 in which aliphatic ester groups are derived from lower aliphatic alcohols having from 1 to 7 carbon atoms, araliphatic ester components are derived from monocyclic-lower aliphatic alcohols having from 1 to 7 carbon atoms in the aliphatic moiety, aromatic ester components are derived from $C_{1-7}$-alkoxy-, $C_{1-7}$-alkylamino- or di-($C_{1-7}$)-alkylamino- or halo-phenols and heterocyclic ester groups are derived from tetrahydrofuranol or tetrahydropyranol, and salts of such compounds having at least one salt-forming group.

30. Esters according to claim 21 in which the substituents in the ester components are free, esterified or etherified hydroxy groups, esterified groups being derived from aliphatic carboxylic acids having from 1 to 7 carbon atoms and etherified groups being derived from aliphatic alcohols having from 1 to 7 carbon atoms, and salts of such compounds having at least one salt-forming group.

31. Esters according to claim 27 in which the α-carboxy group of the respective amino acid is esterified, and salts of such compounds having at least one salt-forming group.

32. Mono-, di-, tri-, tetra-, penta-, hexa- and nona-esters according to claim 27, and salts of such compounds having at least one salt-forming group.

33. Amides according to claim 1 in which the amide group is unsubstituted or is derived from a cyclic or acyclic, primary or secondary amine, the hydrocarbon radical or radicals substituting the amine nitrogen atom being, in the case of the acyclic amines, alkyl groups having from 1 to 7 carbon atoms and, in the case of the cyclic amines, alkylene groups having from 2 to 6 carbon atoms, and salts of such compounds having at least one salt-forming group.

34. Amides according to claim 15 in which the amide group is unsubstituted or is derived from a cyclic or acyclic, primary or secondary amine, the hydrocarbon radical or radicals substituting the amine nitrogen atom being, in the case of the acyclic amines, alkyl groups having from 1 to 7 carbon atoms and, in the case of the cyclic amines, alkylene groups having from 2 to 6 carbon atoms, and salts of such compounds having at least one salt-forming group.

35. Amides according to claim 19 in which the amide group is unsubstituted or is derived from a cyclic or acyclic, primary or secondary amine, the hydrocarbon radical or radicals substituting the amine nitrogen atom being, in the case of the acyclic amines, alkyl groups having from 1 to 7 carbon atoms and, in the case of the cyclic amines, alkylene groups having from 2 to 6 carbon atoms, and salts of such compounds having at least one salt-forming group.

36. Amides according to claim 25 in which the amide group is unsubstituted or is derived from a cyclic or acyclic, primary or secondary amine, the hydrocarbon radical or radicals substituting the amine nitrogen atom being, in the case of the acyclic amines, alkyl groups having from 1 to 7 carbon atoms and, in the case of the cyclic amines, alkylene groups having from 2 to 6 carbon atoms, and salts of such compounds having at least one salt-forming group.

37. Mono-, di-, tri-, tetra-, penta-, hexa- and nona-amides according to claim 33, and salts of such compounds having at least one salt-forming group.

38. Compounds according to claim 1 in which in formula (I) the radical Kw in the radical As° is an unsubstituted alkylene or alkylidene radical having from 2 to 6 carbon atoms, and salts of such compounds having at least one salt-forming group.

39. Compounds according to claim 12 in which in formula (I) the radical Kw in the radical As° is an unsubstituted alkylene or alkylidene radical having from 2 to 6 carbon atoms, and salts of such compounds having at least one salt-forming group.

40. Compounds according to claim 14 in which in formula (I) the radical Kw in the radical As° is an unsubstituted alkylene or alkylidene radical having from 2 to 6 carbon atoms, and salts of such compounds having at least one salt-forming group.

41. Compounds according to claim 18 in which in formula (I) the radical Kw in the radical As° is an unsubstituted alkylene or alkylidene radical having from 2 to 6 carbon atoms, and salts of such compounds having at least one salt-forming group.

42. Compounds according to claim 1 in which Kw represents methylene, di-, tri- or tetra-methylene, ethylidene, propylidene, 2,2-dimethylethylidene, butylidene, 3,3-dimethylpropylidene, or pentylidene, and salts of such compounds having at least one salt-forming group.

43. Compounds according to claim 20 in which Kw represents methylene, di-, tri- or tetra-methylene, ethylidene, propylidene, 2,2-dimethylethylidene, butylidene, 3,3-dimethylpropylidene, or pentylidene, and salts of such compounds having at least one salt-forming group.

44. Compounds according to claim 23 in which As° represents the radical of D- or L-lactic acid, of glycine, alanine, α-aminobutyric acid, valine, norvaline, leucine, isoleucine, norleucine or of corresponding amino acids of the D-series, and salts of such compounds having at least one salt-forming group.

45. Compounds according to claim 24 in which As° represents the radical of D- or L-lactic acid, of glycine, alanine, α-aminobutyric acid, valine, norvaline, leucine, isoleucine, norleucine or of corresponding amino acids of the D-series, and salts of such compounds having at least one salt-forming group.

46. Compounds according to claim 25 in which As° represents the radical of D- or L-lactic acid, of glycine, alanine, α-aminobutyric acid, valine, norvaline, leucine, isoleucine, norleucine or of corresponding amino acids of the D-series, and salts of such compounds having at least one salt-forming group.

47. Compounds according to claim 1 in which in formula (I), in the peptide sequence n=0, and salts of such compounds having at least one salt-forming group.

48. Compounds according to claim 16 in which in formula (I), in the peptide sequence n=0, and salts of such compounds having at least one salt-forming group.

49. Compounds according to claim 25 in which in formula (I), in the peptide sequence n=0, and salts of such compounds having at least one-salt forming group.

50. Compounds according to claim 1, in which the peptide sequence in formula (I) is selected from the group consisting of -Ala-D-Glu, -Ala-D-Glu-NH$_2$, -Ala-D-Glu(NH$_2$), -Ala-D-Glu-D-Ala-NH$_2$, -Ala-D-Glu(NH$_2$)-NH$_2$, -Ala-D-Glu(Ala), -Ala-D-Glu(NH$_2$)-D-Ala-NH$_2$ and -Ala-D-Glu(Ala)-NH$_2$, or in which the peptide sequence represents a corresponding sequence in which -Gly-, -Ser-, -Abu-, -Leu-, -αMeAla- or -Val- stand in place of the first alanine radical, and salts of such compounds having at least one salt-forming group.

51. Compounds according to claim 15 in which the peptide sequence in formula (I) is selected from the group consisting of -Ala-D-Glu, -Ala-D-Glu-NH$_2$, -Ala-D-Glu(NH$_2$), -Ala-D-Glu-D-Ala-NH$_2$, -Ala-D-Glu(NH$_2$)-NH$_2$, -Ala-D-Glu(Ala), -Ala-D-Glu(NH$_2$)-D-Ala-NH$_2$ and -Ala-D-Glu(Ala)-NH$_2$, or in which the peptide sequence represents a corresponding sequence in which -Gly-, -Ser-, -Abu-, -Leu-, -αMeAla- or -Val- stand in place of the first alanine radical, and salts of such compounds having at least one salt-forming group.

52. Compounds according to claim 23 in which the peptide sequence in formula (I) is selected from the group consisting of -Ala-D-Glu, -Ala-D-Glu-NH$_2$, -Ala-D-Glu(NH$_2$), -Ala-D-Glu-D-Ala-NH$_2$, -Ala-D-Glu(NH$_2$)-NH$_2$, -Ala-D-Glu(Ala), -Ala-D-Glu(NH$_2$)-D-Ala-NH$_2$ and -Ala-D-Glu(Ala)-NH$_2$, or in which the peptide sequence represents a corresponding sequence in which -Gly-, -Ser-, -Abu-, -Leu-, -αMeAla- or -Val- stand in place of the first alanine radical, and salts of such compounds having at least one salt-forming group.

53. Compounds according to claim 1 in which the peptide sequence in formula (I) is selected from the group consisting of -As°-Ala-D-Glu, -As°-Ala-D-Glu-NH$_2$, -As°-Ala-D-Glu(NH$_2$), As°-Ala-D-Glu-D-Ala-NH$_2$, As°-Ala-D-Glu(NH$_2$)-NH$_2$, As°-Ala-D-Glu(Ala), As°-Ala-D-Glu(NH$_2$)-D-Ala-NH$_2$ and As°-Ala-D-Glu(Ala)-NH$_2$, wherein As° represents the radical of D- or L-alanine, D- or L-lactic acid, glycolic acid or glycine, and salts of such compounds having at least one salt-forming group.

54. Compounds according to claim 15 in which the peptide sequence in formula (I) is selected from the group consisting of -As°-Ala-D-Glu, -As°-Ala-D-Glu-NH$_2$, -As°-Ala-D-Glu(NH$_2$), As°-Ala-D-Glu-D-Ala-NH$_2$, As°-Ala-D-Glu(NH$_2$)-NH$_2$, As°-Ala-D-Glu(Ala), As°-Ala-D-Glu(NH$_2$)-D-Ala-NH$_2$ and As°-Ala-D-Glu(Ala)-NH$_2$, wherein As° represents the radical of D- or L-alanine, D- or L-lactic acid, glycolic acid or glycine, and salts of such compounds having at least one salt-forming group.

55. Compounds according to claim 23 in which the peptide sequence in formula (I) is selected from the group consisting of -As°-Ala-D-Glu, -As°-Ala-D-Glu-NH$_2$, -As°-Ala-D-Glu(NH$_2$), As°-Ala-D-Glu-D-Ala-NH$_2$, As°-Ala-D-Glu(NH$_2$)-NH$_2$, As°-Ala-D-Glu(Ala), As°-Ala-D-Glu(NH$_2$)-D-Ala-NH$_2$ and As°-Ala-D-Glu(Ala)-NH$_2$, wherein As° represents the radical of D- or L-alanine, D- or L-lactic acid, glycolic acid or glycine, and salts of such compound having at least one salt-forming group.

56. Compounds according to claim 1, that have the R configuration of the ** asymmetry centre in formula (I), in which the radicals $R_a^1$-CO-, $R_b^1$-CO- and $R^2$-CO- have from 8 to 16 carbon atoms and, in the case of $R^2$-CO-, from 2 to 16 carbon atoms, and that have a peptide sequence selected from the group consisting of -Ala-D-Glu, -Ala-D-Glu-NH$_2$, -Ala-D-Glu(NH$_2$), -Ala-D-Glu-D-Ala-NH$_2$, -Ala-D-Glu(NH$_2$)-NH$_2$, -Ala-D-Glu(Ala), -Ala-D-Glu(NH$_2$)-D-Ala-NH$_2$, -Ala-D-Glu(Ala)-NH$_2$, -As°-Ala-D-Glu, -As°-Ala-D-Glu-NH$_2$, -As°-Ala-D-Glu(NH$_2$), As°-Ala-D-Glu-D-Ala-NH$_2$, As°-Ala-D-Glu(NH$_2$)-NH$_2$, As°-Ala-D-Glu(Ala), As°-Ala-D-Glu(NH$_2$)-D-Ala-NH$_2$ and As°-Ala-D-Glu(Ala)-NH$_2$, and salts of such compounds having at least one salt-forming group.

57. Compounds according to claim 18 that have the R configuration at the ** asymmetry centre in formula (I), in which the radicals $R_a^1$-CO-, $R_b^1$-CO- and $R^2$-CO- have from 8 to 16 carbon atoms and, in the case of $R^2$-CO-, from 2 to 16 carbon atoms, and that have a peptide sequence selected from the group consisting of -Ala-D-Glu, -Ala-D-Glu-NH$_2$, -Ala-D-Glu(NH$_2$), -Ala-D-Glu-D-Ala-NH$_2$, -Ala-D-Glu(NH$_2$)-NH$_2$, -Ala-D-GLu(Ala), -Ala-D-Glu(NH$_2$)-D-Ala-NH$_2$, -Ala-D-Glu(Ala)-NH$_2$, -As°-Ala-D-Glu, -As°-Ala-D-Glu-NH$_2$, -As°-Ala-D-Glu(NH$_2$), As°-Ala-D-Glu-D-Ala-NH$_2$, As°-Ala-D-Glu(NH$_2$)-NH$_2$, As°-Ala-D-Glu(Ala), As°-Ala-D-Glu(NH$_2$)-D-Ala-NH$_2$ and As°-Ala-D-Glu(Ala)-NH$_2$, and salts of such compounds having at least one salt-forming group.

58. Compounds according to claim 23 that have the R configuration at the ** asymmetry centre in formula (I), in which the radicals $R_a^1$-CO-, $R_b^1$-CO- and $R^2$-CO- have from 8 to 16 carbron atoms and, in the case of $R^2$-CO-, from 2 to 16 carbon atoms, and that have a peptide sequence selected from the group consisting of -Ala-D-Glu, -Ala-D-Glu-NH$_2$, -Ala-D-Glu(NH$_2$), -Ala-D-Glu-D-Ala-NH$_2$, -Ala-D-Glu(NH$_2$)-NH$_2$, -Ala-D-Glu(Ala), -Ala-D-Glu(NH$_2$)-D-Ala-NH$_2$, -Ala-D-Glu(Ala)-NH$_2$, -As°-Ala-D-Glu, -As°-Ala-D-Glu-NH$_2$, -As°-Ala-D-Glu(NH$_2$), As°-Ala-D-Glu-D-Ala-NH$_2$, As°-Ala-D-Glu(NH$_2$)-NH$_2$, As°-Ala-D-Glu(Ala), As°-Ala-D-Glu(NH$_2$)-D-Ala-NH$_2$ and As°-Ala-D-Glu(Ala)-NH$_2$, and salts of such compounds having at least one salt-forming group.

59. Compounds according to claim 56 in which the acyl radicals $R_a^1$-CO- and $R_b^1$-CO- are different from $R^2$-CO- and represent the radical of caprylic, capric, lauric, myristic, palmitic, stearic or oleic acid, and salts of such compounds having at least one salt-forming group.

60. A lipopeptide according to claim 1, selected from the group consisting of palmitoyl-Cys(2[R], 3-dilauroyloxy-propyl)-Ala-D-Glu-NH$_2$, palmitoyl-Cys(2[R], 3-dipalmitoyloxy-propyl)-Ala-D-Glu(Ala)-NH$_2$, palmitoyl-Cys(2[R], 3-dilauroyloxy-propyl)-Ala-D-Glu(NH$_2$), palmitoyl-Cys(2[R], 3-dilauroyloxy-propyl)-Abu-D-Glu-NH$_2$, palmitoyl-Cys(2-[R], 3-dilauroyloxy-propyl)-Ala-D-Glu(NH$_2$)-OnBu, palmitoyl-Cys(2[R], 3-dilauroyloxy-propyl)-Ala-D-Glu(OnBu)-NH$_2$, palmitoyl-Cys(2[R], 3-dilauroyloxy-propyl)-D-Ala-Ala-D-Glu-NH$_2$,

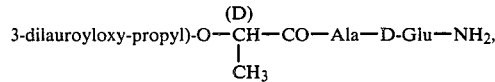

palmitoyl-Cys(2[R], 3-dilauroyloxy-propyl)-O-CH$_2$CO-Ala-D-Glu-NH$_2$, palmitoyl-Cys(2[R], 3-dilauroyloxy-propyl)-Ala-D-Glu(NH$_2$)-O-CH$_2$-O-CO-C(CH$_3$)$_3$, palmitoyl-Cys(2[R], 3-dilauroyloxy-propyl)-Ser-D-Glu(OCH$_3$)-OCH$_3$, palmitoyl-Cys(2[R], 3-dilauroyloxy-propyl)-Ala-D-Gla-NH$_2$,
palmitoyl-Cys(2[R], 3-dilauroyloxy-propyl)-Abu-D-Glu,
palmitoyl-Cys(2[R], 3-dilauroyloxy-propyl)-Val-D-Glu-NH$_2$,
palmitoyl-Cys(2[R], 3-dilauroyloxy-propyl)-αMeAla-D-Glu-NH$_2$,
palmitoyl-Cys(2[R], 3-dilauroyloxy-propyl)-Ala-D-Glu-(Lys-OCH$_3$)-NH$_2$, palmitoyl-Cys(2[R], 3-dilauroyloxy-propyl)-Ala-D-Glu(Lys-Lys-OCH$_3$)-NH$_2$,
palmitoyl-Cys(2[R], 3-dilauroyloxy-propyl)-Ala-D-Glu(Arg), the mono- and di-methyl ester and mono- and di-amide thereof, palmitoyl-Cys(2[R]),

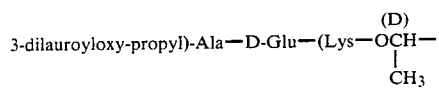

the mono- and di-methyl ester and mono- and di-amide thereof,
and corresponding lipopeptides in which, instead of palmitoyl there is present at the nitrogen of the cysteine radical lauroyl, caprinoyl, capryloyl or myristoyl, and compounds corresponding to these and to the above-listed lipopeptides in which there are present in the diacyloxypropyl radical instead of lauroyl radicals the radicals of palmitic, caprylic, capric and myristic acid, and the compounds corresponding to all of these lipopeptides in which the configuration at the chiral atom of the diacyloxypropyl radical is S instead of R, and corresponding diastereoisomeric mixtures of R and S compounds, as well as, optionally, the unsubstituted or substituted amides thereof, and salts of such compounds having at least one salt-forming group.

61. Compounds according to claim 1, namely the esters of aliphatic alcohols having from 1 to 7 carbon atoms or the esters of $C_{1-7}$-alkanoyloxymethyl alcohols, $C_{1-7}$-alkanoyloxyethyl alcohols, ($C_{3-8}$-cycloalkyl)-carbonyl-oxymethyl alcohols, ($C_{3-8}$-cycloalkyl)-carbonyloxyethyl alcohols, propyleneglycol, glycerin, or of a $C_{1-7}$-alkoxy-, $C_{1-7}$-alkylamino-, di-($C_{1-7}$-alkyl)-amino- or halo-phenol of one of the lipopeptides selected from the group consisting of
palmitoyl-Cys(2[R], 3-dipalmitoyloxy-propyl)-Ala-D-Glu(Ala)-NH$_2$,
palmitoyl-Cys(2[R], 3-dilauroyloxy-propyl)-Ala-D-Glu(NH$_2$),
palmitoyl-Cys(2[R], 3-dilauroyloxy-propyl)-Abu-Glu-NH$_2$,
palmitoyl-Cys(2[R], 3-dilauroyloxy-propyl)-Ala-D-Glu(NH$_2$)-OnBu,
palmitoyl-Cys(2[R], 3-dilauroyloxy-propyl)-Ala-D-Glu(OnBu)-NH$_2$,
palmitoyl-Cys(2[R], 3-dilauroyloxy-propyl)-D-Ala-Ala-D-Glu-NH$_2$, palmitoyl-Cys(2[R]),

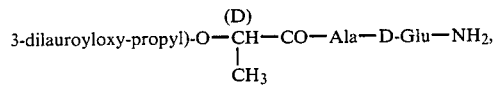

palmitoyl-Cys(2[R], 3-dilauroyloxy-propyl)-O-CH$_2$CO-Ala-D-Glu-NH$_2$,
palmitoyl-Cys(2[R], 3-dilauroyloxy-propyl)-Ala-D-Glu(NH$_2$)-O-CH$_2$-O-CO-C(CH$_3$)$_3$,
palmitoyl-Cys(2[R], 3-dilauroyloxy-propyl)-Ser-D-Glu(OCH$_3$)-OCH$_3$,
palmitoyl-Cys(2[R], 3-dilauroyloxy-propyl)-Ala-D-Gla-NH$_2$,
palmitoyl-Cys(2[R], 3-dilauroyloxy-propyl)-Abu-D-Glu,
palmitoyl-Cys(2[R], 3-dilauroyloxy-propyl)-Val-D-Glu-NH$_2$,
palmitoyl-Cys(2[R], 3-dilauroyloxy-propyl)-αMeAla-D-Glu-NH$_2$,
palmitoyl-Cys(2[R], 3-dilauroyloxy-propyl)-Ala-D-Glu-(Lys-OCH$_3$)-NH$_2$,
palmitoyl-Cys(2[R], 3-dilauroyloxy-propyl)-Ala-D-Glu(Lys-Lys-OCH$_3$)-NH$_2$,
palmitoyl-Cys(2[R], 3-dilauroyloxy-propyl)-Ala-D-Glu(Arg), palmitoyl-Cys(2[R]),

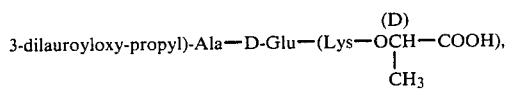

and corresponding lipopeptides in which, instead of palmitoyl there is present at the nitrogen of the cysteine radical lauroyl, caprinoyl, capryloyl or myristoyl, and compounds corresponding to these and to the above-listed lipopeptides in which there are present in the diacyloxypropyl radical instead of lauroyl radicals the radicals of palmitic, caprylic, capric and myristic acid, and the compounds corresponding to all of these lipopeptides in which the configuration at the chiral atom of the diacyloxypropyl radical is S instead of R, and corresponding diastereoisomeric mixtures of R and S compounds.

62. Compounds according to claim 1, namely substituted amides or amides of $C_{1-7}$-alkylamines, pyrrolidine, piperidine or piperazine of one of the lipopeptides selected from the group consisting of
palmitoyl-Cys(2[R], 3-dipalmitoyloxy-propyl)-Ala-D-Glu(Ala)-NH$_2$,
palmitoyl-Cys(2[R], 3-dilauryloxy-propyl)-Ala-D-Glu(NH$_2$),
palmitoyl-Cys(2[R], 3-dilauroyloxy-propyl)-Abu-D-Glu-NH$_2$,
palmitoyl-Cys(2[R], 3-dilauroyloxy-propyl)-Ala-D-Glu(NH$_2$)-OnBu,
palmitoyl-Cys(2[R], 3-dilauroyloxy-propyl)-Ala-D-Glu(OnBu)-NH$_2$,
palmitoyl-Cys(2[R], 3-dilauroyloxy-propyl)-D-Ala-Ala-D-Glu-NH$_2$, palmitoyl-Cys(2[R]),

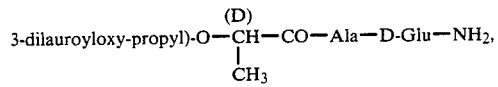

palmitoyl-Cys(2[R], 3-dilauroyloxy-propyl)-O-CH$_2$CO-Ala-D-Glu-NH$_2$,
palmitoyl-Cys(2[R], 3-dilauroyloxy-propyl)-Ala-D-Glu(NH$_2$)-O-CH$_2$-O-CO-C(CH$_3$)$_3$, palmitoyl-Cys(2[R], 3-dilauroyloxy-propyl)-Ser-D-Glu(OCH₃)-OCH₃,
palmitoyl-Cys(2[R], 3-dilauroyloxy-propyl)-Ala-D-Gla-NH₂,
palmitoyl-Cys(2[R], 3-dilauroyloxy-propyl)-Abu-D-Glu,
palmitoyl-Cys(2[R], 3-dilauroyloxy-propyl)-Val-D-Glu-NH₂,
palmitoyl-Cys(2[R], 3-dilauroyloxy-propyl)-αMeAla-D-Glu-NH₂,
palmitoyl-Cys(2[R], 3-dilauroyloxy-propyl)-Ala-D-Glu-(Lys-OCH₃)-NH₂,
palmitoyl-Cys(2[R], 3-dilauroyloxy-propyl)-Ala-D-Glu(Lys-Lys-OCH₃)-NH₂,
palmitoyl-Cys(2[R], 3-dilauroyloxy-propyl)-Ala-D-Glu(Arg), palmitoyl-Cys(2[R],

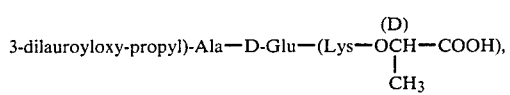

(D)
3-dilauroyloxy-propyl)-Ala—D-Glu—(Lys—OCH—COOH),
$\qquad\qquad\qquad\qquad\qquad\qquad\qquad\qquad$ |
$\qquad\qquad\qquad\qquad\qquad\qquad\qquad\qquad$ CH₃ and corresponding lipopeptides in which, instead of palmitoyl there is present at the nitrogen of the cysteine radical lauroyl, caprinoyl, capryloyl or myristoyl, and compounds corresponding to these and to the above-listed lipopeptides in which there are present in the diacyloxypropyl radical instead of lauroyl radicals the radicals of palmitic, caprylic, capric and myristic acid, and the compounds corresponding to all of these lipopeptides in which the configuration at the chiral atom of the diacyloxypropyl radical is S instead of R, and corresponding diastereoisomeric mixtures of R and S compounds.

63. A lipopeptide according to claim 1 selected from the group consisting of
lauroyl-Cys(2[R,S], 3-didecanoyloxy-propyl)-Ala-D-Glu-NH₂,
decanoyl-Cys(2[R,S], 3-dilauroyloxy-propyl)-Ala-D-Glu-NH₂,
myristoyl-Cys(2[R,S], 3-dilauryloxy-propyl)-Ala-D-Glu-NH₂,
palmitoyl-Cys(2[R,S], 3-didecanoyloxy-propyl)-Ala-D-Glu-NH₂,
palmitoyl-Cys(2[R,S], 3-didecanoyloxy-propyl)-Abu-D-Glu(OCH₃)-OCH₃, and of the esters
of aliphatic alcohols having from 1 to 7 carbon atoms or the esters of $C_{1-7}$-alkanoyloxymethyl alcohols, $C_{1-7}$-alkanoyloxyethyl alcohols, ($C_{3-8}$-cycloalkyl)-carbonyloxymethyl alcohols, ($C_{3-8}$-cycloalkyl)-carbonyloxyethyl alcohols, propyleneglycol, glycerin, or of a $C_{1-7}$-alkoxy-, $C_{1-7}$-alkylamino-, di-($C_{1-7}$-alkyl)-amino- or halo-phenol and unsubstituted amides or amides of $C_{1-7}$-alkylamines, pyrrolidine, piperidine or piperazine thereof.

64. Compounds according to claim 1, namely ammonium salts, alkali or alkaline earth salts of one of the acidic lipopeptides claimed in claim 1 and pharmaceutically acceptable non-toxic acid addition salts of the basic lipopeptides mentioned in claim 1.

65. Palmitoyl-Cys(2[R], 3-dilauroyloxy-propyl)-Ala-D-Glu{Lys-Lys-OMe}-NH₂ or a pharmaceutically acceptable acid addition salt thereof according to claim 1.

66. Palmitoyl-Cys(2[R], 3-dilauroyloxy-propyl)-Ala-D-Glu(Gly-taurine-sodium salt)-NH₂ according to claim 1.

67. Decanoyl-Cys(2[R,S], 3-dioctanoyloxy-propyl)-Ala-D-Glu-NH₂ or a pharmaceutically acceptable salt thereof according to claim 1.

68. Palmitoyl-Cys(2[R], 3-dilauroyloxy-propyl)-Abu-D-Glu-NH₂ or a pharmaceutically acceptable salt thereof according to claim 1.

69. Palmitoyl-Cys(2[R], 3-dilauroyloxy-propyl)-Ala-D-Glu(Arg-OMe)-NH₂ or a pharmaceutically acceptable salt thereof according to claim 1.

70. Palmitoyl-Cys(2[R], 3-dilauroyloxy-propyl)-Ala-D-Gla-NH₂ or a pharmaceutically acceptable salt thereof according to claim 1.

71. Palmitoyl-Cys(2[R], 3-dilauroyloxy-propyl)-Abu-D-Glu or a pharmaceutically acceptable salt thereof according to claim 1.

72. A lipopeptide of the formula I according to claim 1 in which the center of asymmetry designated by ** has the R-configuration, each of the radicals $R_a^1$-CO- and $R_b^1$-CO- represents lauroyl; $R^2$-CO- represents palmitoyl; n represents zero; $As^1$ represents alanine or α-amino-butyric acid; $Z^1$ represents amino or hydroxy; $Z^2$ represents hydroxy or the N-terminal radical of arginine-methylester, lysyllysine-methylester or lysyl-D-alanine; and $Z^3$ represents hydrogen or carboxy; or a pharmaceutically acceptable salt thereof.

73. A lipopeptide of the formula I according to claim 1 in which the center of asymmetry designated by ** has the R-configuration, each of the radicals $R_a^1$-CO- and $R_b^1$-CO- represents lauroyl; $R^2$-CO- represents palmitoyl; n represents zero; $As^1$ represents alanine or α-aminobutyric acid; $Z^1$ represents amino or hydroxy; $Z^2$ represents the N-terminal radical of glycyl-taurine or alanyl-taurine; and $Z^3$ represents hydrogen; or a pharmaceutically acceptable salt thereof.

74. Pharmaceutical preparations for enteral or parenteral (including nasal and vaginal) administration to warm-blooded animals including humans containing an amount effective for stimulating immunity of a compound as defined in claim 1 together with a significant amount of a pharmaceutical carrier.

75. Pharmaceutical preparations according to claim 74 for parenteral (including nasal and vaginal) administration to warm-blooded animals including humans suffering from tumour.

76. Method of treating warm-blooded animals including humans suffering from tumour by enterally or parenterally administrating an effective dose of a compound as defined in claim 1.

77. Method for the prophylaxis or treatment of bacterial infections in warm-blooded animals including humans by administering an effective dose of a compound as defined in claim 1.

* * * * *